US008905961B2

(12) United States Patent
Braido et al.

(10) Patent No.: US 8,905,961 B2
(45) Date of Patent: Dec. 9, 2014

(54) SYSTEMS, APPARATUSES, AND METHODS FOR CARDIOVASCULAR CONDUITS AND CONNECTORS

(75) Inventors: Peter N. Braido, Maple Grove, MN (US); Yousef F. Alkhatib, Maple Grove, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 733 days.

(21) Appl. No.: 12/340,280

(22) Filed: Dec. 19, 2008

(65) Prior Publication Data

US 2010/0160847 A1 Jun. 24, 2010

(51) Int. Cl.
*A61M 5/00* (2006.01)
*A61F 2/86* (2013.01)
(Continued)

(52) U.S. Cl.
CPC . *A61F 2/064* (2013.01); *A61F 2/89* (2013.01); *A61F 2/06* (2013.01); *A61F 2/848* (2013.01);
(Continued)

(58) Field of Classification Search
CPC .................. A61F 2/2409; A61F 2002/30364; A61F 2002/30392; A61F 2/06; A61F 2/07; A61F 2/064; A61F 2/86; A61F 2/88; A61F 2/89; A61F 2/90; A61F 2/91; A61F 2/915; A61F 2002/07; A61F 2002/072; A61F 2002/075; A61F 2002/077; A61F 2/848
USPC .............. 600/16, 36; 623/1.1, 3.1, 3.3, 23.64, 623/23.72, 23.76, 900, 2.39, 2.38, 2.4, 623/2.41; 604/8
See application file for complete search history.

(56) References Cited

U.S. PATENT DOCUMENTS 3,859,668 A * 1/1975 Anderson ..................... 623/2.39
3,996,623 A * 12/1976 Kaster .......................... 623/2.39
(Continued)

FOREIGN PATENT DOCUMENTS

WO 9802099 A1 1/1998
WO 9918887 A1 4/1999
(Continued)

OTHER PUBLICATIONS

Aeba, R., et al., "Apico-Pulmonary Artery Conduit Repair of Congenitally Corrected Transposition of the Great Arteries With Ventricular Septal Defect and Pulmonary Outflow Tract Obstruction: A 10-Year Follow-Up," Ann Thorac Surg, 2003, 76:1383-8 (Pages).
(Continued)

*Primary Examiner* — Adam Marcetich
(74) *Attorney, Agent, or Firm* — Holland & Hart

(57) ABSTRACT

A cardiovascular conduit system may comprise a connector. The connector may comprise a proximal end adapted to attach to a cardiovascular organ. The proximal end may comprise a first plurality of expandable members, and each member in the first plurality of expandable members may be deployable from a delivery position to a deployed position. The first plurality of expandable members may be dimensioned to deploy inside the cardiovascular organ to secure the connector to the cardiovascular organ. The connector may comprise a distal end adapted to attach to a conduit and an opening extending through the connector. Connectors for cardiovascular conduit systems may also include expandable stents. Connectors may be rotatably secured to a conduit, and the conduit may be reinforced. Methods for forming and using cardiovascular conduit systems are also disclosed.

28 Claims, 27 Drawing Sheets

(51) Int. Cl.
| | | |
|---|---|---|
| *A61F 2/90* | (2013.01) | |
| *A61F 2/04* | (2013.01) | |
| *A61F 2/06* | (2013.01) | |
| *A61F 2/89* | (2013.01) | |
| *A61F 2/848* | (2013.01) | |
| *A61F 2/88* | (2006.01) | |
| *A61B 17/11* | (2006.01) | |
| *A61F 2/07* | (2013.01) | |
| *A61B 17/00* | (2006.01) | |
| *A61F 2/24* | (2006.01) | |
| *A61F 2/92* | (2013.01) | |

(52) U.S. Cl.
CPC ... *A61F 2/86* (2013.01); *A61F 2/88* (2013.01); *A61F 2002/072* (2013.01); *A61B 17/11* (2013.01); *A61B 2017/00252* (2013.01); *A61B 2017/00867* (2013.01); *A61B 2017/1135* (2013.01); *A61F 2/07* (2013.01); *A61F 2/24* (2013.01); *A61F 2/92* (2013.01)
USPC .......... 604/8; 604/9; 623/1.1; 623/1.12; 623/1.15; 623/1.16; 623/1.17; 623/1.18; 623/1.22; 623/1.28; 623/1.51; 623/1.53

(56) References Cited

U.S. PATENT DOCUMENTS

| | | | | |
|---|---|---|---|---|
| 4,366,581 A | * | 1/1983 | Shah | 623/2.41 |
| 4,366,819 A | * | 1/1983 | Kaster | 606/153 |
| 4,397,617 A | | 8/1983 | Sergio et al. | |
| 4,769,031 A | | 9/1988 | McGough et al. | |
| 4,787,386 A | | 11/1988 | Walsh et al. | |
| 4,790,844 A | | 12/1988 | Ovil | |
| 4,816,029 A | | 3/1989 | Penny, III et al. | |
| 4,872,874 A | | 10/1989 | Taheri | |
| 5,330,528 A | | 7/1994 | Lazim | |
| 5,332,403 A | | 7/1994 | Kolff | |
| 5,466,216 A | | 11/1995 | Brown et al. | |
| 5,466,242 A | * | 11/1995 | Mori | 606/198 |
| 5,511,958 A | | 4/1996 | Chen et al. | |
| 5,599,173 A | | 2/1997 | Chen et al. | |
| 5,725,552 A | * | 3/1998 | Kotula et al. | 606/213 |
| 5,755,770 A | | 5/1998 | Ravenscroft | |
| 5,766,240 A | * | 6/1998 | Johnson | 623/2.39 |
| 5,776,185 A | | 7/1998 | Verona et al. | |
| 5,782,860 A | * | 7/1998 | Epstein et al. | 606/213 |
| 5,810,708 A | | 9/1998 | Woodard et al. | |
| 5,843,179 A | * | 12/1998 | Vanney et al. | 623/2.38 |
| 5,846,261 A | * | 12/1998 | Kotula et al. | 606/213 |
| 5,871,537 A | | 2/1999 | Holman et al. | |
| 5,876,436 A | * | 3/1999 | Vanney et al. | 623/2.39 |
| 5,931,842 A | | 8/1999 | Goldsteen et al. | |
| 5,941,908 A | | 8/1999 | Goldsteen et al. | |
| 5,965,086 A | | 10/1999 | Rose et al. | |
| 5,972,017 A | | 10/1999 | Berg et al. | |
| 5,976,178 A | | 11/1999 | Goldsteen et al. | |
| 6,001,056 A | | 12/1999 | Jassawalla et al. | |
| 6,001,124 A | | 12/1999 | Bachinski | |
| 6,007,544 A | * | 12/1999 | Kim | 606/108 |
| 6,007,574 A | * | 12/1999 | Pulnev et al. | 623/1.15 |
| 6,013,190 A | | 1/2000 | Berg et al. | |
| 6,016,810 A | | 1/2000 | Ravenscroft | |
| 6,036,702 A | | 3/2000 | Bachinski et al. | |
| 6,048,362 A | | 4/2000 | Berg | |
| 6,059,823 A | | 5/2000 | Holman et al. | |
| 6,068,654 A | | 5/2000 | Berg et al. | |
| 6,074,416 A | | 6/2000 | Berg et al. | |
| 6,113,612 A | | 9/2000 | Swanson et al. | |
| 6,120,432 A | | 9/2000 | Sullivan et al. | |
| 6,136,007 A | | 10/2000 | Goldsteen et al. | |
| 6,146,325 A | | 11/2000 | Lewis et al. | |
| 6,152,937 A | | 11/2000 | Peterson et al. | |
| 6,152,945 A | | 11/2000 | Bachinski et al. | |
| 6,152,956 A | | 11/2000 | Pierce | |
| 6,162,244 A | * | 12/2000 | Braun et al. | 623/1.12 |
| 6,176,864 B1 | * | 1/2001 | Chapman | 606/153 |
| 6,186,942 B1 | | 2/2001 | Sullivan et al. | |
| 6,186,986 B1 | | 2/2001 | Berg et al. | |
| 6,200,260 B1 | | 3/2001 | Bolling | |
| 6,206,912 B1 | | 3/2001 | Goldsteen et al. | |
| 6,235,054 B1 | | 5/2001 | Berg et al. | |
| 6,261,315 B1 | | 7/2001 | St. Germain et al. | |
| 6,273,880 B1 | | 8/2001 | Berg et al. | |
| 6,273,917 B1 | * | 8/2001 | Inoue | 623/23.64 |
| 6,293,965 B1 | | 9/2001 | Berg et al. | |
| 6,299,575 B1 | | 10/2001 | Bolling | |
| 6,302,905 B1 | | 10/2001 | Goldsteen et al. | |
| 6,309,416 B1 | | 10/2001 | Swanson et al. | |
| 6,319,276 B1 | | 11/2001 | Holman et al. | |
| 6,346,071 B1 | | 2/2002 | Mussivand | |
| 6,352,554 B2 | | 3/2002 | De Paulis | |
| 6,358,278 B1 | * | 3/2002 | Brendzel et al. | 623/2.39 |
| 6,371,982 B2 | | 4/2002 | Berg et al. | |
| 6,387,037 B1 | | 5/2002 | Bolling et al. | |
| 6,390,969 B1 | | 5/2002 | Bolling et al. | |
| 6,416,527 B1 | | 7/2002 | Berg et al. | |
| 6,428,464 B1 | | 8/2002 | Bolling | |
| 6,428,550 B1 | * | 8/2002 | Vargas et al. | 606/153 |
| 6,432,131 B1 | | 8/2002 | Ravenscroft | |
| 6,440,163 B1 | | 8/2002 | Swanson et al. | |
| 6,443,884 B1 | | 9/2002 | Miyawaki | |
| 6,450,171 B1 | | 9/2002 | Buckberg et al. | |
| 6,451,033 B1 | | 9/2002 | Berg et al. | |
| 6,451,048 B1 | * | 9/2002 | Berg et al. | 623/1.13 |
| 6,475,222 B1 | | 11/2002 | Berg et al. | |
| 6,508,252 B1 | | 1/2003 | Berg et al. | |
| 6,508,822 B1 | | 1/2003 | Peterson et al. | |
| 6,511,491 B2 | | 1/2003 | Grudem et al. | |
| 6,514,196 B1 | | 2/2003 | Sullivan et al. | |
| 6,533,812 B2 | | 3/2003 | Swanson et al. | |
| 6,599,303 B1 | | 7/2003 | Peterson et al. | |
| 6,610,004 B2 | | 8/2003 | Viole et al. | |
| 6,620,176 B1 | | 9/2003 | Peterson et al. | |
| 6,669,720 B1 | * | 12/2003 | Pierce | 623/1.13 |
| 6,673,084 B1 | | 1/2004 | Peterson et al. | |
| 6,692,523 B2 | | 2/2004 | Holman et al. | |
| 6,702,829 B2 | | 3/2004 | Bachinski et al. | |
| 6,726,648 B2 | | 4/2004 | Kaplon et al. | |
| 6,746,463 B1 | | 6/2004 | Schwartz | |
| 6,749,598 B1 | | 6/2004 | Keren et al. | |
| 6,773,453 B2 | | 8/2004 | Ravenscroft | |
| 6,802,806 B2 | | 10/2004 | McCarthy et al. | |
| 6,805,692 B2 | | 10/2004 | Muni et al. | |
| 6,863,677 B2 | | 3/2005 | Breznock | |
| 6,889,082 B2 | | 5/2005 | Bolling et al. | |
| 6,920,882 B2 | | 7/2005 | Berg et al. | |
| 6,926,689 B2 | | 8/2005 | Scheule | |
| 6,960,219 B2 | | 11/2005 | Grudem et al. | |
| 6,994,666 B2 | | 2/2006 | Shannon et al. | |
| 7,025,773 B2 | | 4/2006 | Gittings et al. | |
| 7,029,483 B2 | | 4/2006 | Schwartz | |
| 7,048,681 B2 | | 5/2006 | Tsubouchi et al. | |
| 7,077,801 B2 | | 7/2006 | Haverich | |
| 7,094,248 B2 | | 8/2006 | Bachinski et al. | |
| 7,182,771 B1 | | 2/2007 | Houser et al. | |
| 2001/0004675 A1 | | 6/2001 | Woodard et al. | |
| 2001/0027287 A1 | | 10/2001 | Shmulewitz et al. | |
| 2001/0049553 A1 | | 12/2001 | De Paulis | |
| 2002/0040235 A1 | | 4/2002 | Holman et al. | |
| 2002/0045846 A1 | | 4/2002 | Kaplon et al. | |
| 2002/0099437 A1 | * | 7/2002 | Anson et al. | 623/1.15 |
| 2002/0128703 A1 | | 9/2002 | Ravenscroft | |
| 2002/0173809 A1 | | 11/2002 | Fleischman et al. | |
| 2002/0173836 A1 | * | 11/2002 | Pinchuk | 623/1.12 |
| 2002/0183834 A1 | * | 12/2002 | Klaco | 623/2.4 |
| 2002/0198603 A1 | | 12/2002 | Buckberg et al. | |
| 2003/0040765 A1 | | 2/2003 | Breznock | |
| 2003/0083679 A1 | | 5/2003 | Grudem et al. | |
| 2003/0083738 A1 | | 5/2003 | Holman et al. | |
| 2003/0139800 A1 | * | 7/2003 | Campbell | 623/1.15 |
| 2003/0176830 A1 | | 9/2003 | Scheule | |
| 2003/0208257 A1 | | 11/2003 | Holman et al. | |
| 2003/0212418 A1 | * | 11/2003 | Yencho et al. | 606/153 |

(56) References Cited

U.S. PATENT DOCUMENTS

| | | | |
|---|---|---|---|
| 2003/0220684 A1 | 11/2003 | Holman et al. | |
| 2004/0049264 A1* | 3/2004 | Sowinski et al. | 623/1.28 |
| 2004/0059178 A1* | 3/2004 | McCarthy et al. | 600/16 |
| 2004/0078053 A1* | 4/2004 | Berg et al. | 606/213 |
| 2004/0082910 A1 | 4/2004 | Constantz et al. | |
| 2004/0092973 A1* | 5/2004 | Chanduszko et al. | 606/151 |
| 2004/0097900 A1 | 5/2004 | Keren et al. | |
| 2004/0106931 A1* | 6/2004 | Guiles et al. | 606/108 |
| 2004/0162608 A1 | 8/2004 | Haverich | |
| 2004/0176836 A1* | 9/2004 | Kari et al. | 623/1.32 |
| 2004/0181126 A1 | 9/2004 | Buckberg et al. | |
| 2004/0193004 A1 | 9/2004 | Tsubouchi et al. | |
| 2004/0199191 A1 | 10/2004 | Schwartz | |
| 2004/0210202 A1 | 10/2004 | Weinstein | |
| 2004/0215321 A1 | 10/2004 | Holman et al. | |
| 2005/0085842 A1* | 4/2005 | Eversull et al. | 606/191 |
| 2005/0119688 A1 | 6/2005 | Bergheim | |
| 2005/0149093 A1 | 7/2005 | Pokorney | |
| 2005/0154411 A1 | 7/2005 | Breznock et al. | |
| 2005/0209502 A1 | 9/2005 | Schmid et al. | |
| 2005/0251187 A1 | 11/2005 | Beane et al. | |
| 2005/0256363 A1 | 11/2005 | Bolling et al. | |
| 2005/0261759 A1 | 11/2005 | Lambrecht et al. | |
| 2006/0014999 A1 | 1/2006 | Heilman et al. | |
| 2006/0030747 A1 | 2/2006 | Kantrowitz et al. | |
| 2006/0030933 A1* | 2/2006 | DeLegge et al. | 623/1.19 |
| 2006/0036313 A1 | 2/2006 | Vassiliades | |
| 2006/0074271 A1* | 4/2006 | Cotter | 600/16 |
| 2006/0079736 A1 | 4/2006 | Chin et al. | |
| 2006/0089707 A1* | 4/2006 | Vassiliades et al. | 623/1.23 |
| 2006/0155364 A1* | 7/2006 | Holloway et al. | 623/1.16 |
| 2006/0161133 A1 | 7/2006 | Laird et al. | |
| 2006/0161193 A1 | 7/2006 | Beane et al. | |
| 2006/0259050 A1* | 11/2006 | De Winter | 606/153 |
| 2007/0112380 A1* | 5/2007 | Figulla et al. | 606/213 |
| 2007/0142879 A1* | 6/2007 | Greenberg et al. | 607/62 |
| 2007/0167980 A1* | 7/2007 | Figulla et al. | 606/213 |
| 2007/0198078 A1* | 8/2007 | Berra et al. | 623/1.12 |
| 2008/0140108 A1* | 6/2008 | Matsuura et al. | 606/192 |
| 2008/0288054 A1* | 11/2008 | Pulnev et al. | 623/1.22 |
| 2009/0076531 A1* | 3/2009 | Richardson et al. | 606/153 |
| 2009/0082778 A1* | 3/2009 | Beane et al. | 606/108 |
| 2009/0105816 A1* | 4/2009 | Olsen et al. | 623/2.37 |
| 2010/0160832 A1 | 6/2010 | Braido | |
| 2010/0160939 A1 | 6/2010 | Braido | |
| 2010/0161040 A1 | 6/2010 | Braido | |
| 2011/0009951 A1* | 1/2011 | Bogert | 623/1.22 |

FOREIGN PATENT DOCUMENTS

| | | | |
|---|---|---|---|
| WO | 0027313 | A2 | 5/2000 |
| WO | 0100108 | A1 | 1/2001 |
| WO | 0112074 | A1 | 2/2001 |
| WO | 02058594 | A1 | 8/2002 |
| WO | 2004000093 | A2 | 12/2003 |

OTHER PUBLICATIONS

Behrendt, D., et al., "Relief of left ventricular outflow tract obstruction in infants and small children with valved extra cardiac conduits," Ann Thorac Surg., 1987; 43(1):82-6 (Pages).

Bickers, G., et al., "Gastroesophageal deformities of left ventricular-abdominal aortic conduit," AJR Am J Roentgenol, May 1982; 138(5):867-9 (Pages).

Marino, S. Bradley, et al., "Early Results of the Ross Procedure in Simple and Complex Left Heart Disease," Circulation, 1999; 10:II-162-6 (Pages).

Brown, J., et al., "Long-Term Results of Apical Aortic Conduits in Children With Complex Left Ventricular Outflow Tract Obstruction," Ann Thorac Surg., 2005; 80:2301-8 (Pages).

Ugorji, C., et al., "Post-Traumatic Apical Left Ventricular Aneurysm in a Patient with Left Ventricular Apical-Abdominal Aortic Conduit: Case Presentation," Cardiovascular Diseases, Bulletin of the Texas Heart Institute, 1979; 6:4 (Pages).

Crestanello, J., et al., "Is there a role for the left ventricle apical-aortic conduit for acquired aortic stenosis?", J Heart Valve Dis. Jan. 2004; 13(1):57-62; discussion 62-3 (Pages).

Cooley, Denton, A., et al., "Left Ventricle to Abdominal Aorta Conduit for Relief of Aortic Stenosis," Cardiovascular Diseases, Bulleting of the Texas Heart Institute, 1975, 2; 3 (Pages).

Fogel, M., et al, "Evaluation and follow-up of patients with left ventricular apical to aortic conduits with 2D and 3D magnetic resonance imaging and Doppler echocardiography: A new look at an old operation," American Heart Journal, 2001; 141:630-6 (Pages).

Frommelt, P., et al., "Natural history of apical left ventricular to aortic conduits in pediatric patients," Circulation, Nov. 1991; 84(5Suppl):III213-8 (Pages).

Gammie, J., et al., "Aortic valve bypass for the high-risk patient with aortic stenosis," Annals of Thoracic Surgery, 2006; 81:1605-1611 ( Pages).

Koul, B., et al., "Aortoventriculoplasty ad modum Konno. Experience with five cases," Scand J. Thorac Cardiovasc Surg., 1984; 18(3):239-42 (Pages).

Misbach, G., et al., "Left ventricular outflow enlargement by the Konno procedure," Journal of Thoracic Cardiovascular Surgery, Nov. 1982; 84(5):696-703 (Pages).

Miyawaki, F., et al., "Recovery directed left ventricular assist deVice; a new concept," Asaio J, May-Jun. 2000; 46(3):361-6 (Pages).

Norwood WI, et al., "Management of infants with left ventricular outflow obstruction by conduit interposition between the ventricular apex and thoracic aorta," J Thorac Cardiovasc Surg., Nov. 1983; 86(5):771-6 (Pages).

Rocchini, A., et al., "Clinical and hemodynamic follow-up of left ventricular to aortic conduits in patients with aortic stenosis," J Am Coll Cardiol., Apr. 1983; 1(4):1135-43 (Pages).

Serraf, A., et al., "Surgical Treatment of Subaortic Stenosis: A Seventeen-Year Experience," J Thorac Cardiovasc Surg., 1999; 117:669-78 (Pages).

Vassiliades, T., "Off-pump apicoaortic conduit insertion for high-risk patients with aortic stenosis," European Journal of Cardio-thoracic Surgery, 2003; 23:156-8 (Pages).

Vigano, M., et al., "Modified method for Novacor left ventricular assist device implantation," Ann Thorac Surg., Jan. 1996; 61(1):247-9 (Pages).

PCT International Search Report for International Application No. PCT/US2009/006565, mailed Jun. 11, 2010 (5 pp.).

* cited by examiner

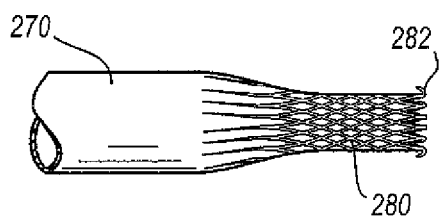
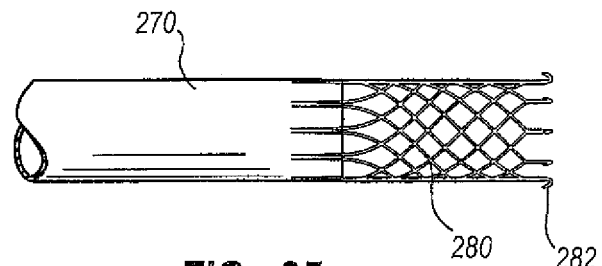
FIG. 34　　　　　　　　FIG. 35
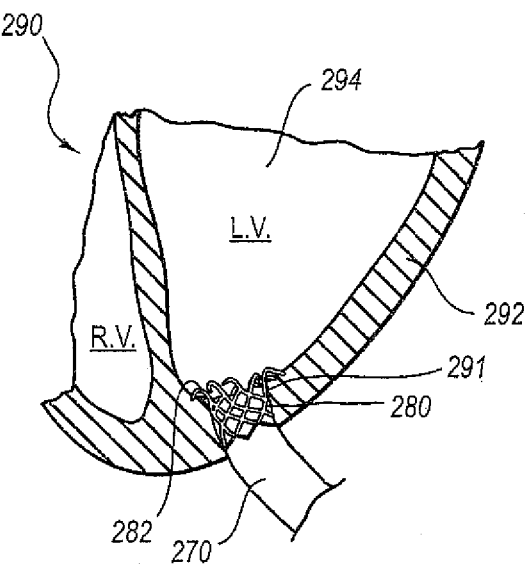
FIG. 36
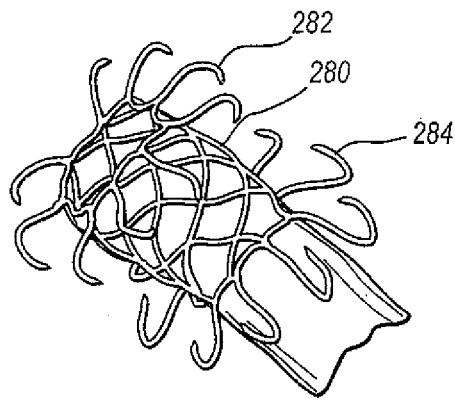
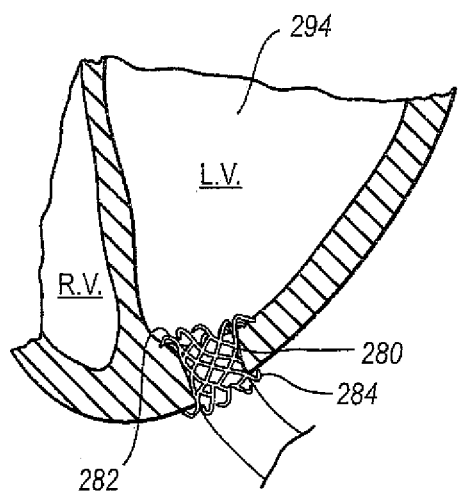
FIG. 37　　　　　　　　FIG. 38

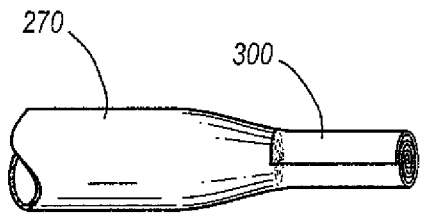 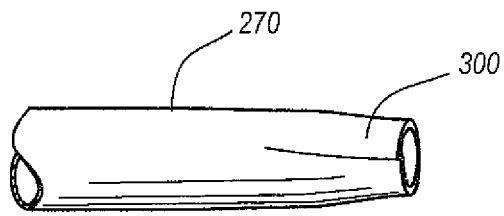
FIG. 39  FIG. 40
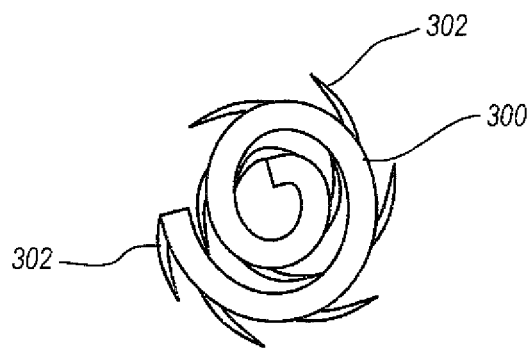
FIG. 41
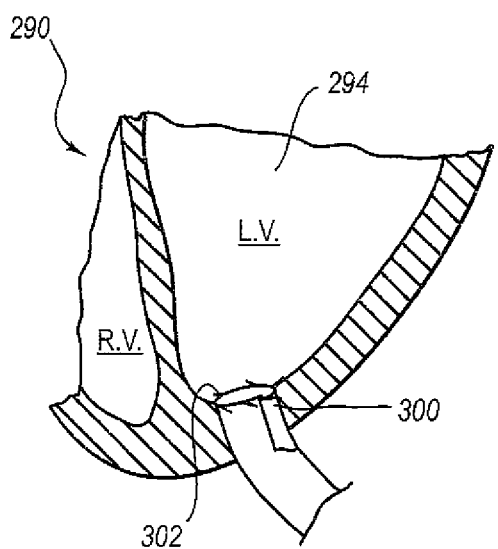
FIG. 42

SYSTEMS, APPARATUSES, AND METHODS FOR CARDIOVASCULAR CONDUITS AND CONNECTORS

BACKGROUND

Aortic valve replacement is a cardiac surgery procedure that replaces a patient's aortic valve with a prosthetic valve. Aortic valve replacement typically requires open heart surgery, which may be risky and/or impractical for many patients. Aortic valve replacement may not be an option for patients with aortic stenosis, left ventricular outflow obstruction, a heavily calcified ascending aorta, a heavily calcified aortic root, and/or other high risk medical conditions. For example, patients with conditions that preclude a median sternotomy may not be candidates for an aortic valve replacement operation.

Apical aortic conduits may provide a less invasive alternative to aortic valve replacement. An apical aortic conduit may be connected between the apex of the heart and the aorta in a procedure similar to a coronary artery bypass graft. Apical aortic conduits may improve blood flow between the heart and the aorta by bypassing a diseased or malfunctioning aortic valve. Patients who are not eligible for aortic valve replacement may be treated by using an apical aortic conduit to bypass the valve. For example, apical aortic conduits may be used in pediatric patients. The native valve may be left in place in pediatric patients to eliminate the need for periodic valve replacements as the patient grows. Thus, the apical aortic conduit may maintain the maximum possible function of the native valve while bypassing the restricted flow to lessen stress on the heart and allow more blood flow to the body. In other words, the apical aortic conduit may bypass the native valve to allow for extra flow to the aorta while still allowing the maximum flow that the native valve can physiologically handle.

Traditional apical aortic conduits may fail or malfunction for various reasons. For example, the conduit material used in an apical aortic conduit may become blocked as a result of kinking. Traditional conduits may also become occluded and obstruct apical flow. Also, apical aortic conduits are typically sutured to the heart and the aorta, and the suturing may cause aneurysms at or near the attachment site. Apical aortic conduits may also cause gastrointestinal complications such as dysphagia and gastric erosion.

SUMMARY

In certain embodiments, a cardiovascular conduit system may comprise a connector. The connector may comprise a proximal end adapted to attach to a cardiovascular organ. The proximal end may comprise a first plurality of expandable members. Each member in the first plurality of expandable members may be deployable from a delivery position to a deployed position, and the first plurality of expandable members may be dimensioned to deploy inside the cardiovascular organ to secure the connector to the cardiovascular organ. The connector may also include a distal end adapted to attach to a conduit and an opening extending through the connector. The opening may be dimensioned to transfer blood between the conduit and the cardiovascular organ.

According to various embodiments, the cardiovascular conduit system may further comprise a retractable retaining member that holds the first plurality of expandable members in the delivery position. In at least one embodiment, the first plurality of expandable members may be spaced around a perimeter of the proximal end of the connector. According to some embodiments, the first plurality of expandable members may comprise at least one of: shape-memory wire, shape-memory tube, or shape-memory sheet.

The cardiovascular conduit system may comprise fabric extending between at least two expandable members in the first plurality of expandable members. In some embodiments, at least one member in the first plurality of expandable members may comprise a barb. According to certain embodiments, the connector may comprise an apical connector.

In various embodiments, the connector may further comprise a mid-section between the distal and proximal ends and a second plurality of expandable members extending from the mid-section. Each member in the second plurality of expandable members may be deployable from a delivery position to a deployed position, and the second plurality of expandable members may be dimensioned to deploy outside the cardiovascular organ to secure the connector to the cardiovascular organ. According to some embodiments, at least one member in the second plurality of expandable members may be longer than at least one member in the first plurality of expandable members.

According to certain embodiments, the connector may further comprise an expandable mid-section between the distal and proximal ends. The expandable mid-section may be deployable to apply a radial force on an opening in the cardiovascular organ. In some embodiments, the connector may be dimensioned to attach to a vascular organ. According to at least one embodiment, the first plurality of expandable members may form a cylinder in the delivery position.

In various embodiments, the connector may further comprise a mid-section between the distal and proximal ends. The connector may also comprise a second plurality of expandable members extending from the mid-section. Each member in the second plurality of expandable members may be deployable from a delivery position to a deployed position, and the second plurality of expandable members may be dimensioned to deploy outside the cardiovascular organ to secure the connector to the cardiovascular organ. The second plurality of expandable members may form a cylinder in the delivery position.

In at least one embodiment, each member in the first plurality of expandable members may form a spiral in the delivery position. In some embodiments, the first plurality of expandable members may comprise loops, and at least two expandable members in the first plurality of expandable members may overlap. According to various embodiments, the cardiovascular conduit system may comprise a conduit positioned around the distal end of the connector, and the distal end of the connector may comprise a groove dimensioned to attach to the conduit. The cardiovascular conduit system may also comprise a spring positioned around a first end of the first conduit and seated in the groove of the connector to rotatably secure the conduit to the connector. In some embodiments, the ring may be positioned around the spring and seated in the groove of the connector. According to at least one embodiment, the conduit may be attached to the connector, and the conduit may comprise a duct and a reinforcing member.

In various embodiments, the conduit may be attached to an inside of the opening in the connector. According to some embodiments, the conduit may be attached to an outside of the connector. In at least one embodiment, the connector may comprise at least one of a first cuff adapted to be positioned against an outside surface of the cardiovascular organ and a second cuff adapted to be positioned against an inside surface of the cardiovascular organ.

In certain embodiments, a method may comprise coring an opening in a cardiovascular organ and inserting a connector into the opening in the cardiovascular organ. The connector may comprise a plurality of expandable members. The method may further comprise deploying the plurality of expandable members inside the cardiovascular organ to secure the connector to the cardiovascular organ. In at least one embodiment, deploying the plurality of expandable members may comprise retracting a retaining member.

According to various embodiments, the method may comprise sliding a conduit onto a distal end of the connecting member. A distal end of the connecting member may comprise a groove. The method may also comprise positioning a spring around the conduit and in the groove of the connecting member and positioning a ring around the spring. In at least one embodiment, the conduit may comprise a duct and a reinforcing member.

In certain embodiments, a cardiovascular conduit system may comprise an apical connector. The apical connector may comprise an expandable member, and the expandable member may be deployable from a delivery configuration to a deployed configuration. The expandable member may be adapted to apply radial force to an opening in a heart when deployed. In various embodiments, a first plurality of hooks may extend from a proximal end of the expandable member. According to at least one embodiment, the expandable member may be a rolled stent that deploys by unrolling. In other embodiments, the expandable member may comprise a mesh.

According to various embodiments, the first plurality of hooks may be deployable from a delivery configuration to a deployed configuration. In some embodiments, the apical connector may comprise a second plurality of hooks extending from a distal end of the expandable member, and the second plurality of hooks may be deployable from a delivery configuration to a deployed configuration. According to at least one embodiment, the apical connector may comprise a third plurality of hooks extending from the expandable member between the first plurality of hooks and the second plurality of hooks.

According to certain embodiments, a cardiovascular conduit system may comprise a first connector. The first connector may comprise a proximal end dimensioned to be attached to a first cardiovascular organ and may also comprise a distal end. The cardiovascular conduit system may also comprise a first conduit rotatably attached to the distal end of the first connector. According to at least one embodiment, the first connector may comprise a groove formed in the distal end, and the first conduit may be positioned around an outside of the distal end of the first connector.

The cardiovascular conduit system may comprise a first spring positioned around a first end of the first conduit and seated in the groove of the first connector to rotatably secure the first conduit to the first connector. In at least one embodiment, the cardiovascular conduit system may comprise a ring positioned around the first spring and seated in the groove of the first connector. In some embodiments, the cardiovascular conduit system may comprise a second connector. The second connector may comprise a proximal end dimensioned to be attached to a second cardiovascular organ, a distal end, and a groove formed in the distal end of the second connector. The cardiovascular conduit system may also comprise a second spring positioned around the second end of the first conduit and seated in the groove of the second connector to rotatably secure the first conduit to the second connector. In some embodiments, the first connector may comprise an apical connector and the second connector may comprise an aortic connector.

According to various embodiments, the cardiovascular conduit system may further comprise a second connector. The second connector may comprise a first end, a second end, a first groove formed in the first end of the second connector, and a second groove formed in the second end of the second connector. The cardiovascular conduit system may also comprise a second conduit, a second spring positioned around a second end of the first conduit and seated in the first groove of the second connector to rotatably secure the second connector to the first conduit, and a third spring positioned around a first end of the second conduit and seated in the second groove of the second connector to rotatably secure the second conduit to the second connector.

According to some embodiments, the cardiovascular conduit system may further comprise a third connector. The third connector may comprise a proximal end dimensioned to be attached to a second cardiovascular organ, a distal end, and a groove formed in the distal end of the third connector. The cardiovascular conduit system may comprise a fourth spring positioned around a second end of the second conduit and seated in the groove of the third connector.

In certain embodiments, a method may comprise sliding a first end of a surgically implantable conduit over a cardiovascular connector, the cardiovascular connector comprising a groove in a distal end. The method may also comprise positioning a spring over the surgically implantable conduit and in the groove of the cardiovascular connector. The method may comprise coring an opening in a cardiovascular organ. The method may further comprise attaching the cardiovascular connector to the opening in the cardiovascular organ.

According to various embodiments, the method may comprise positioning a ring over the spring and in the groove of the cardiovascular connector, folding the first end of the surgically implantable conduit over the ring, and suturing the first end of the cardiovascular connector to another portion of the cardiovascular connector to hold the ring and spring in place. In at least one embodiment, attaching the cardiovascular connector to the opening in the cardiovascular organ may comprise deploying an expandable section of the cardiovascular connector inside the cardiovascular organ.

In certain embodiments, a cardiovascular conduit system may comprise a surgically implantable conduit. The surgically implantable conduit may comprise a duct and a reinforcing member attached to the duct. According to at least one embodiment, the reinforcing member may comprise a plurality of disconnected rings attached to the duct. In various embodiments, the reinforcing member may comprise a spiral reinforcing wire attached to the duct. In some embodiments, the reinforcing member may comprise a mesh of reinforcing members. In at least one embodiment, the surgically implantable conduit may be pre-shaped to extend from an apex of a heart to an aorta. In various embodiments, the surgically implantable conduit may be flexible.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are part of the specification. Together with the following description these drawings demonstrate and explain various principles of the instant disclosure.

FIG. 34 is a side view of an exemplary expandable connector according to certain embodiments.

FIG. 35 is a side view of the expandable connector illustrated in FIG. 34 in an deployed configuration.

FIG. 36 is a cross-sectional view of a portion of a heart with the expandable connector illustrated in FIG. 34 attached to the heart.

FIG. 37 is a perspective view of an exemplary expandable connector according to certain embodiments.

FIG. 38 is a cross-sectional view of a portion of a heart with the expandable connector illustrated in FIG. 37 attached to the heart.

FIG. 39 is a side view of an exemplary expandable connector according to certain embodiments.

FIG. 40 is a side view of the expandable connector illustrated in FIG. 39 in a deployed configuration.

FIG. 41 is a top view of the exemplary expandable connector illustrated in FIG. 39 with barbs.

FIG. 42 is a cross-sectional view of a portion of a heart with the expandable connector illustrated in FIG. 41 attached to the heart.

Figure 1:
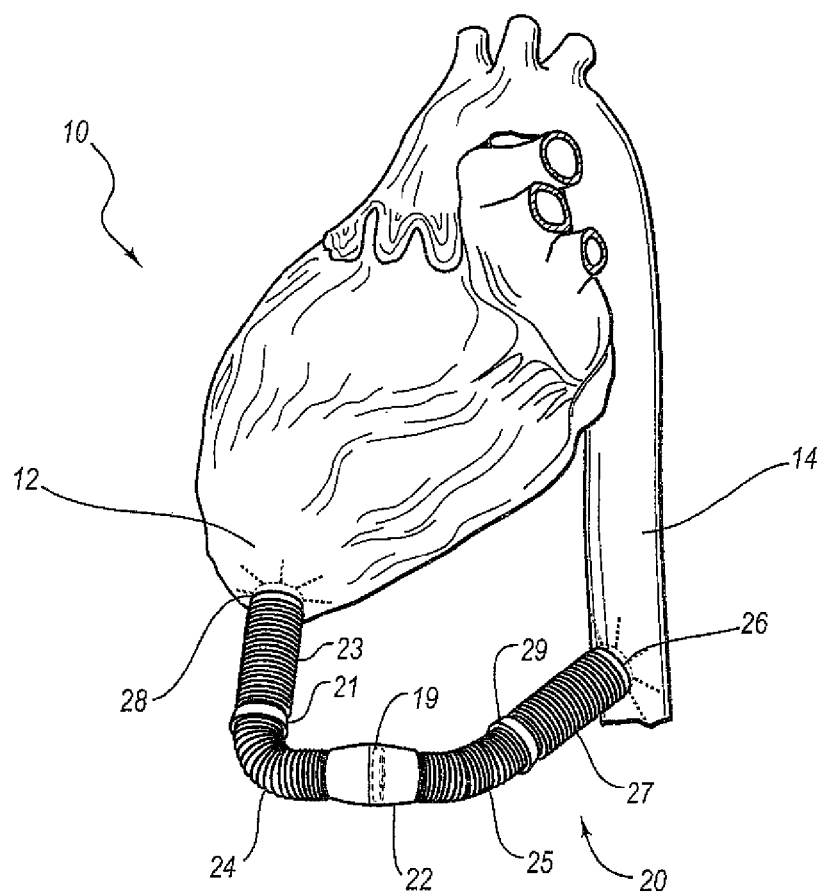
FIG. 1 is a perspective view of an exemplary cardiovascular conduit system attached to a heart according to certain embodiments.

Throughout the drawings, identical reference characters and descriptions indicate similar, but not necessarily identical, elements. While embodiments of the instant disclosure are susceptible to various modifications and alternative forms, specific embodiments have been shown by way of example in the drawings and will be described in detail herein. However, one of skill in the art will understand that embodiments of the instant disclosure are not intended to be limited to the particular forms disclosed herein. Rather, the instant disclosure covers all modifications, equivalents, and alternatives falling within the scope of embodiments defined by the appended claims.

DETAILED DESCRIPTION

A physician may implant a cardiovascular conduit system to circumvent a restriction in blood flow. For example, a physician may use a cardiovascular conduit system to bypass an aortic valve in a patient with aortic valve stenosis. Similarly, a cardiovascular conduit system may be used to bypass a pulmonary valve in a patient with pulmonary valve stenosis. Physicians may also use cardiovascular conduit systems to address various other problems and diseases in a patient's cardiovascular system.

The cardiovascular conduit systems, apparatuses, and methods presented in the instant disclosure may provide various advantages. In some embodiments, physicians may implant a cardiovascular conduit system on a beating heart. Procedures performed on a beating heart may be referred to as off-pump procedures, and off-pump procedures may be less invasive than on-pump procedures (i.e., procedures that require cardiopulmonary bypass). In other embodiments, cardiovascular conduit systems may be used with traditional surgical techniques (e.g., on-pump procedures). In traditional surgical techniques, cardiovascular conduit systems may provide various advantages, such as reduced pump time and smaller incisions. Connectors in a cardiovascular conduit system may be designed to reduce the risk of aneurisms at the attachment site. The conduit in a cardiovascular conduit system may be kink and occlusion resistant. Cardiovascular conduit systems may also reduce the risk of gastrointestinal complications. The following disclosure presents numerous other features and advantages of various cardiovascular conduit systems.

Figure 2:
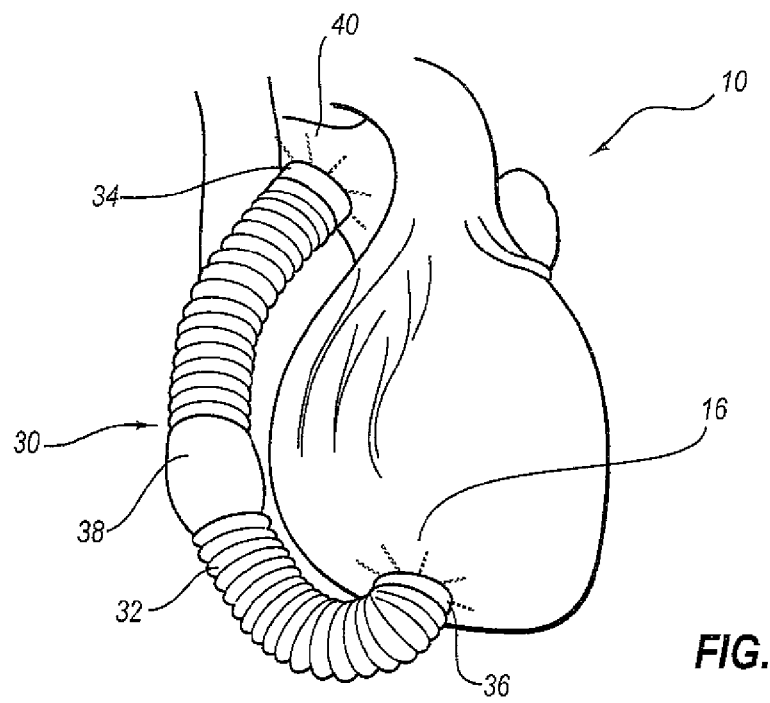
FIG. 2 is a perspective view of an exemplary cardiovascular conduit system attached to a heart according to certain embodiments.

The figures and description of the instant disclosure present various cardiovascular conduit systems, apparatuses, and methods. FIGS. 1 and 2 illustrate cardiovascular conduit systems implanted in a human cardiovascular system. FIGS. 3-48 show exemplary connectors for cardiovascular conduit systems, FIGS. 49-56 show exemplary conduit-connector attachments, and FIGS. 57-61 illustrate exemplary reinforced conduit for cardiovascular conduit systems.

Cardiovascular conduit systems may typically be attached to cardiovascular organs. A cardiovascular organ may be any organ in a cardiovascular system. Cardiovascular organs include the heart and all of the blood vessels (e.g., arteries and veins) in the cardiovascular system. Thus, the aorta and the pulmonary artery may be referred to as cardiovascular organs. According to some embodiments, blood vessels may also be referred to as vascular organs.

FIG. 1 shows a cardiovascular conduit system 20 connecting a left ventricle 12 of a heart 10 to an aorta 14. Conduit system 20 may include a connector 28 attached to an apex of heart 10. Connector 28 may also be attached to a first end of a conduit section 23. Conduit for use in a cardiovascular conduit system, such as conduit section 23, may be referred to as surgically implantable conduit. The conduit section 23 and portion of the connector 28 to which the conduit section 23 is connected are shown positioned outside of the heart 10. A second end of conduit section 23 may be attached to a connector 21, and connector 21 may be attached to a first end of a conduit section 24. A second end of conduit section 24 may be attached to a valve housing 22 that includes a valve 19. Valve 19 may control the flow of blood between left ventricle 12 and aorta 14. Various examples of valves and valve housings are illustrated and described in U.S. patent application Ser. No. 12/340,189, filed on 19 Dec. 2008, and entitled "Cardiovascular Valve and Valve Housing Apparatuses and Systems," the disclosure of which is incorporated in its entirety by reference.

Valve housing 22 may also be connected to a first end of a conduit section 25, and a second end of conduit section 25 may be attached to a connector 29. A first end of a conduit section 27 may be attached to connector 29, and a second end of conduit section 27 may be attached to a connector 26. Connector 26 may attach conduit section 27 to aorta 14. The conduit system shown in FIG. 1 may be referred to as an apical aortic conduit system because it connects an apex of heart 10 (at left ventricle 12) to aorta 14.

FIG. 2 illustrates a cardiovascular conduit system 30 connecting a right ventricle 16 of heart 10 to a pulmonary artery 40. A connector 34 may attach conduit 32 to pulmonary artery 40, and a connector 36 may attach conduit 32 to right ventricle 16. Conduit 32 may include a valve 38 that controls blood flow between right ventricle 16 and pulmonary artery 40.

According to various embodiments, a physician may attach a connector of a cardiovascular conduit system to a cardiovascular organ in an off-pump procedure. Since the heart continues to beat in an off-pump procedure, a physician may need to secure the connector to the cardiovascular organ as quickly as possible after coring an opening in the organ. The connectors illustrated in FIGS. 3-48 may be designed for quick and secure attachment to a cardiovascular organ.

The connectors illustrated in FIGS. 3-48 may be various different shapes and sizes. A physician may measure a patient's aorta or other blood vessel to determine the appropriate size of coring device and/or connector to use in implanting a cardiovascular conduit system in the patient. Various examples of cardiovascular cutting devices and valves are shown and described in U.S. patent application Ser. No. 12/340,431, filed on 19 Dec. 2008, and entitled "Systems, Apparatuses, and Methods for Cardiovascular Cutting Devices and Valves," the disclosure of which is incorporated in its entirety by reference. Various examples of blood vessel measuring devices are illustrated and described in U.S. patent application Ser. No. 12/340,382, filed on 19 Dec. 2008, and entitled "Apparatus and Method for Measuring Blood Vessels," the disclosure of which is incorporated in its entirety by reference.

Figure 3:
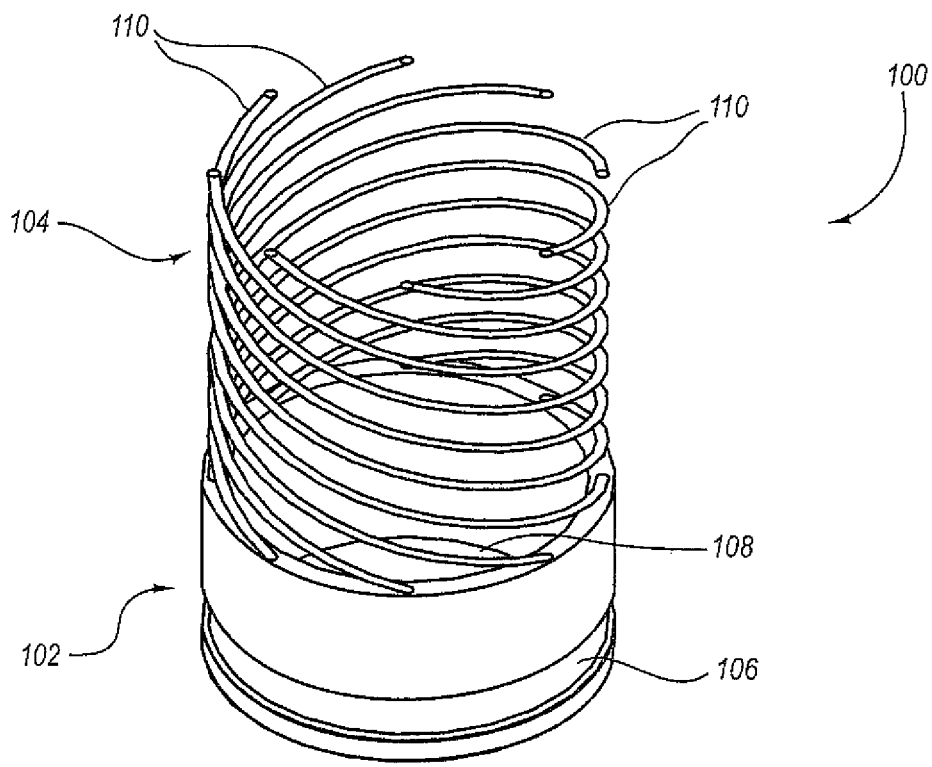
FIG. 3 is a perspective view of an exemplary connector according to certain embodiments.
Figure 4:
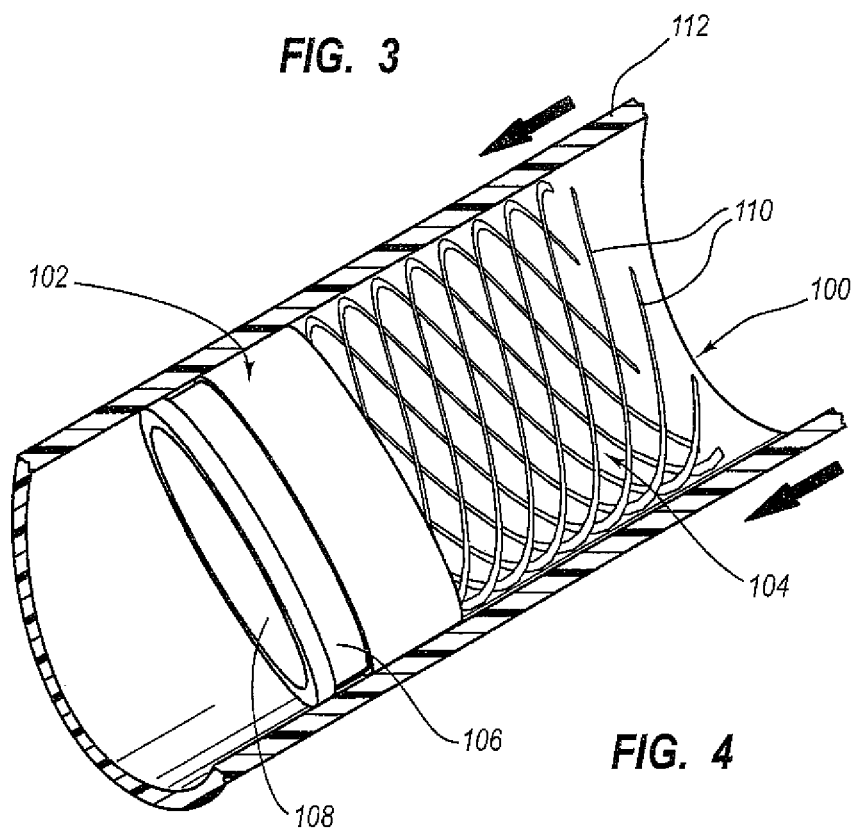
FIG. 4 is a cross-sectional view of an exemplary retaining member on the connector illustrated in FIG. 3.
Figure 5:
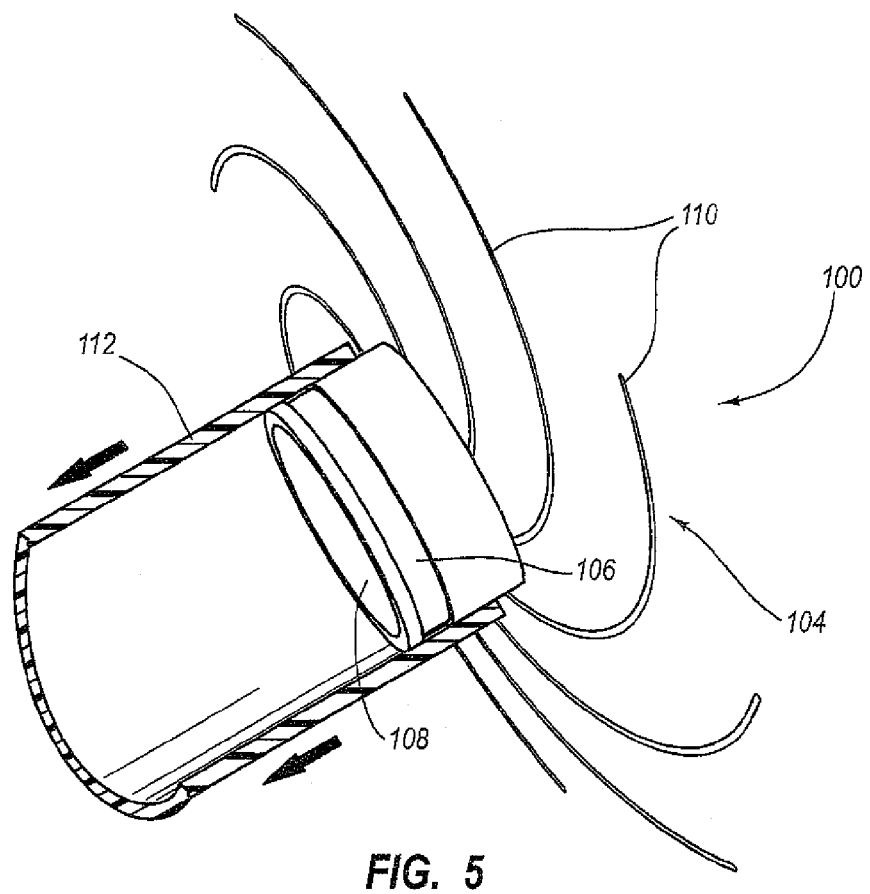
FIG. 5 is a perspective view of the connector illustrated in FIG. 3 in a deployed configuration.
Figure 6:
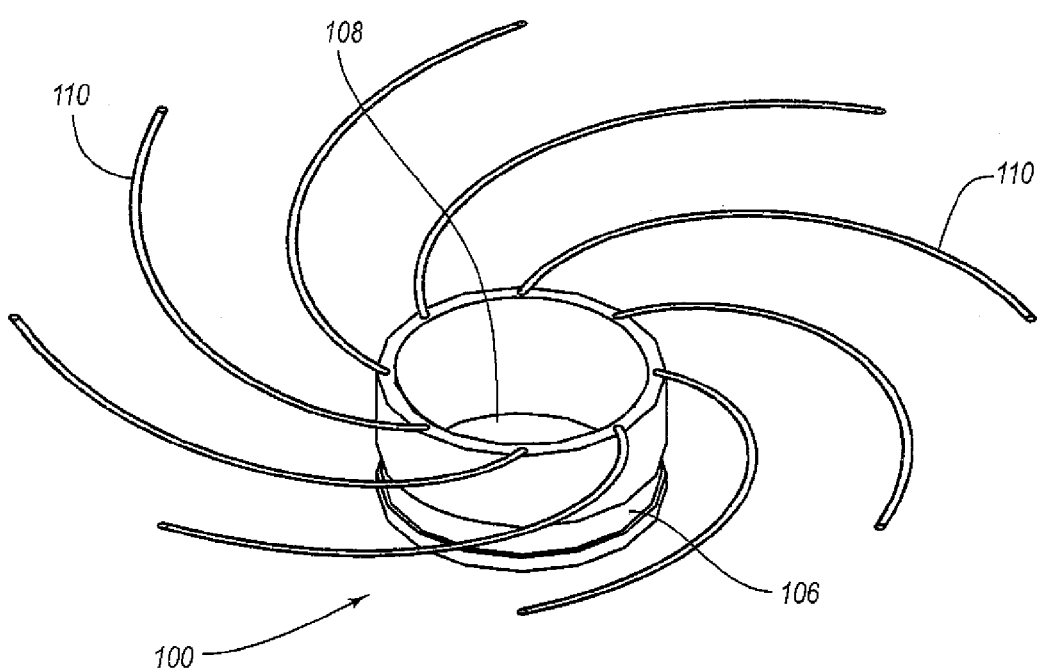
FIG. 6 is another perspective view of the connector illustrated in FIG. 3 in a deployed configuration.

FIGS. 3 and 4 illustrate a connector 100 in a collapsed, delivery configuration. FIGS. 5 and 6 show connector 100 in an expanded, deployed configuration. Connector 100 may have a distal end 102 and a proximal end 104. Proximal end 104 may be adapted to attach to a cardiovascular organ by deploying expandable members 110 inside the cardiovascular organ. Distal end 102 may include a groove 106 adapted to attach to a conduit. The discussion corresponding to FIGS. 49-53 explains how a conduit may be attached to a grooved connector. An opening 108 may extend through connector 100. Opening 108 may be dimensioned to transfer blood between a conduit and a cardiovascular organ.

A delivery configuration may be a connector configuration used for inserting a connector into an opening in a cardiovascular organ. In a delivery configuration, a connector may typically be smaller than in a deployed configuration. Thus, a connector in a delivery configuration may allow for a smaller incision or opening in a cardiovascular organ than a connector in a deployed position.

As shown in FIG. 4, a retractable retaining member, such as sheath 112, may hold connector 100 in a delivery configuration. Sheath 112 may hold connector 100 in a delivery configuration by holding expandable members 110 in a delivery position. Each of expandable members 110 may be spiral-shaped in the delivery position, and together they may form a cylindrical shape. After connector 100 is inserted into an opening in a cardiovascular organ, a physician may retract sheath 112, as shown in FIG. 5. FIG. 6 shows expandable members 110 fully deployed after sheath 112 is removed.

As expandable members 110 deploy, each expandable member may move independently of other expandable members. The independent movement of expandable members 110 may allow expandable members 110 to conform to the shape of the inside of a cardiovascular organ, thereby providing a relatively secure connection to the cardiovascular organ. Expandable members 110 may be spaced evenly around the perimeter of the proximal end 104 of connector 100, as shown in FIGS. 3-6. In some embodiments, expandable members 110 may be spaced unevenly in an asymmetrical manner.

Connector 100 may be made of any suitable material, including metal, plastic, pyrolitic carbon, or any suitable combination of materials. According to some embodiments, connector 100 may be rigid enough to hold open an opening in a cardiovascular organ, but not so rigid that it damages the cardiovascular organ.

In various embodiments, expandable members 110 may be made from a shape-memory material. Shape-memory materials may include, for example, shape-memory alloys, which may also be referred to as smart alloys or memory metals. According to some embodiments, shape-memory materials may exhibit pseudo-elastic and/or super-elastic properties. A shape-memory material may be a copper-zinc-aluminum alloy, a copper-aluminum-nickel alloy, a nickel-titanium alloy (e.g., NITINOL), or any other suitable shape-memory alloy. Expandable members 110 may be made from wires, tubes, or flat sheets of shape-memory material.

Connector 100 may allow for quick and secure attachment of a conduit to a cardiovascular organ without relying on sutures as the primary attachment method. While connector 100 secures itself to a cardiovascular organ from inside the organ, other connectors may include expandable members that secure to the outside of the organ. According to some embodiments, a connector may include expandable members that secure the connector to both the inside and the outside of a cardiovascular organ.

Figure 7:
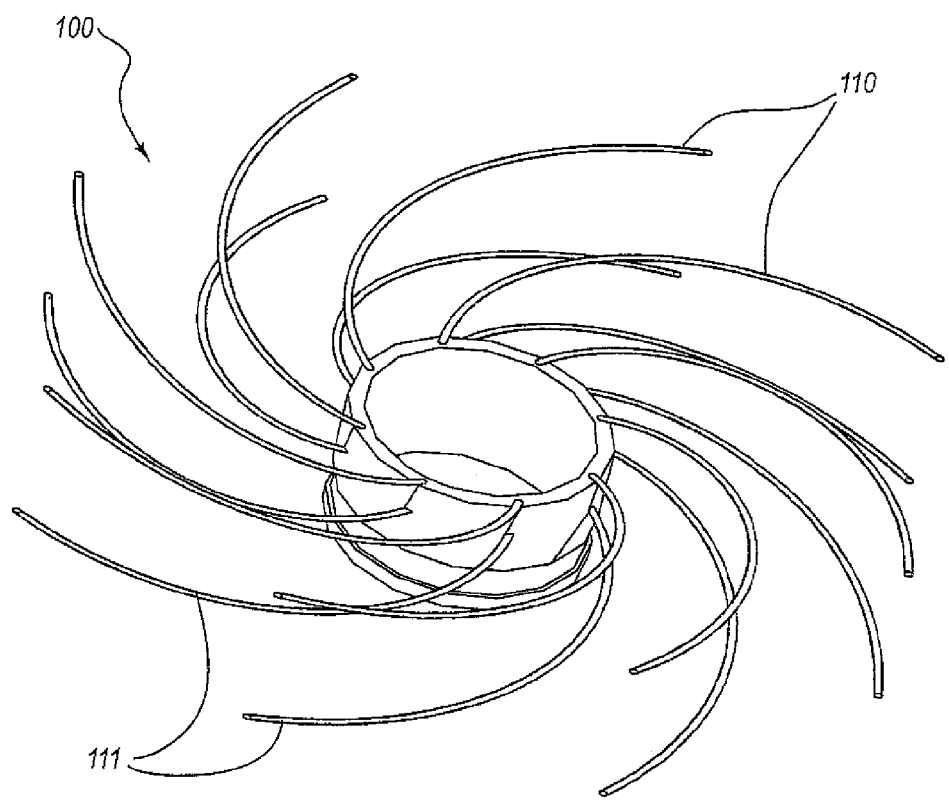
FIG. 7 is a perspective view of the connector illustrated in FIG. 3 with additional expandable members.
Figure 8:
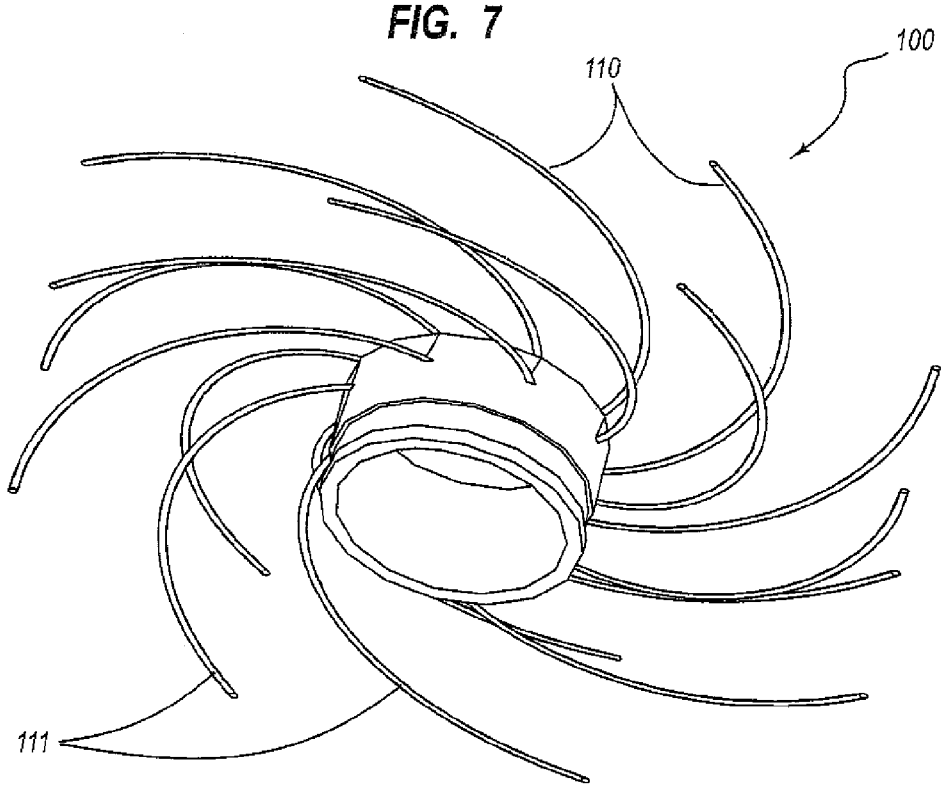
FIG. 8 is another perspective view of the connector illustrated in FIG. 7.

FIGS. 7 and 8 show connector 100 with additional expandable members 111. Expandable members 111 may be designed to be positioned against an external surface of a cardiovascular organ. Thus, connector 100 may attach to a cardiovascular organ by deploying expandable members 110 and 111 on either side of a wall of the cardiovascular organ, in direct contact with the cardiovascular organ to secure the connector 100 to the cardiovascular organ without any interposing material. External expandable members 111 may provide additional security and stability in attaching connector 100 to a cardiovascular organ. In some embodiments, connector 100 may include external expandable members 111 but not internal expandable members 110. External expandable members (i.e., expandable members designed to deploy outside a cardiovascular organ) may also be referred to as distal expandable members, and internal expandable members (i.e., expandable members designed to deploy inside a cardiovascular organ) may also be referred to as proximal expandable members.

Expandable members 110 and 111 may be flexible so that they conform to the anatomy of a cardiovascular organ when they are deployed. Also, the spiral design and flexibility of expandable members 110 and 111 may allow expandable members 110 and 11 to conform to a heart by moving with the heart as the heart expands and contracts.

FIGS. 3-8 illustrate an example configuration of a connector (connector 100) for a cardiovascular conduit system. The design of connector 100 may be referred to as a spiral design. In some embodiments, connectors may have any other suitable design, shape, and/or configuration. For example the opening of a connector may be any suitable shape and/or size and the expandable members of a connector may be any suitable length, size, or configuration. FIGS. 9-48 illustrate various exemplary embodiments of connectors with different shapes and configurations.

Figure 9:
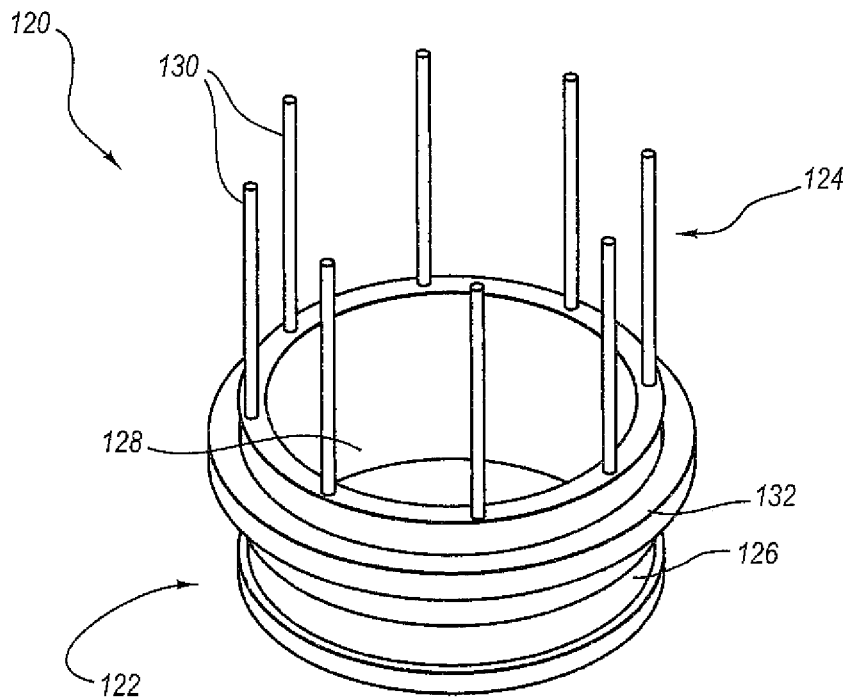
FIG. 9 is a perspective view of an exemplary connector according to certain embodiments.
Figure 10:
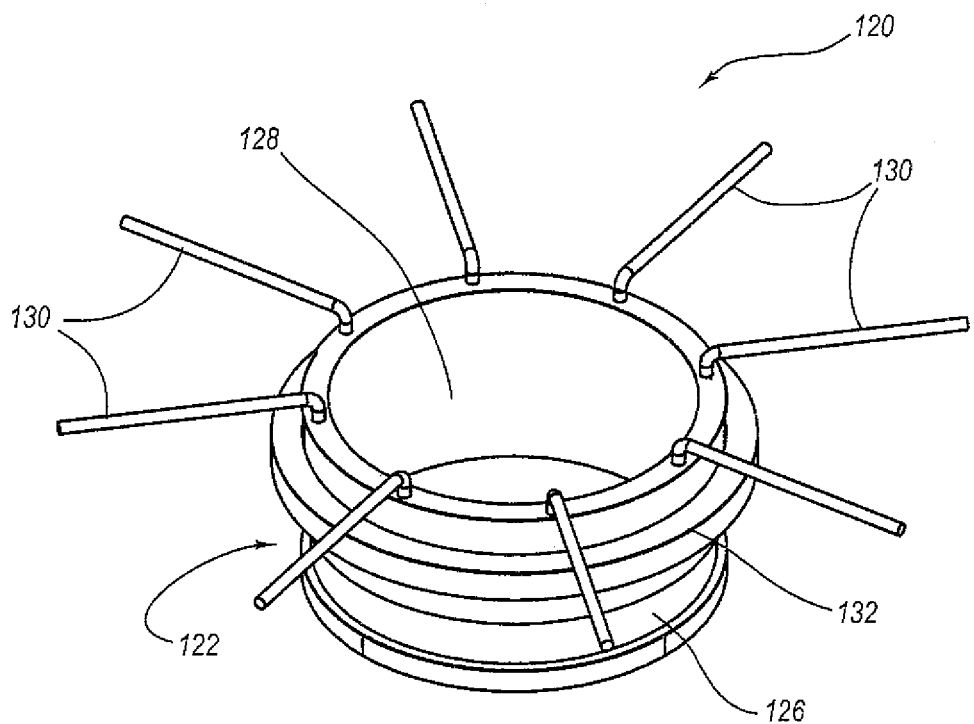
FIG. 10 is a perspective view of the connector illustrated in FIG. 9 in a deployed configuration.

FIGS. 9 and 10 show a connector 120 that includes a distal end 122 a proximal end 124, and an opening 128. Distal end 122 may include a groove 126 for connection to a conduit. Proximal end 124 may include expandable members 130. FIG. 9 shows expandable members 130 in a delivery position, and FIG. 10 shows expandable members 130 in a deployed position. Connector 120 may be referred to as a spider design and may include eight legs (expandable members 100). According to some embodiments, connector 120 may have any suitable number of expandable members, including more or less than eight expandable members.

Connector 120 may also include a cuff 132. In some embodiments, cuff 132 may be made of a material that can be penetrated by a needle to allow a physician to suture cuff 132 to the outside of a cardiovascular organ. Suturing cuff 132 to the cardiovascular organ may help expandable members 130 hold connector 120 in place. In various embodiments, cuff 132 may include openings that allow a physician to suture cuff 132 to a cardiovascular organ. Any of the connectors disclosed herein may include a cuff or other member that allows the connector to be sutured to the cardiovascular organ. The connectors disclosed herein may include cuffs that are designed to be positioned on the outside and/or inside of a cardiovascular organ.

Connector cuffs may be made of fabric or any other suitable material. A cuff may aid in sealing the connector to the cardiovascular organ to minimize blood leakage at the interface between the connector and the cardiovascular organ. A cuff may also promote tissue in-growth that may result in a layer of tissue encapsulating the connector, which may further reduce leakage and may strengthen the connection between the connector and the cardiovascular organ.

Figure 11:
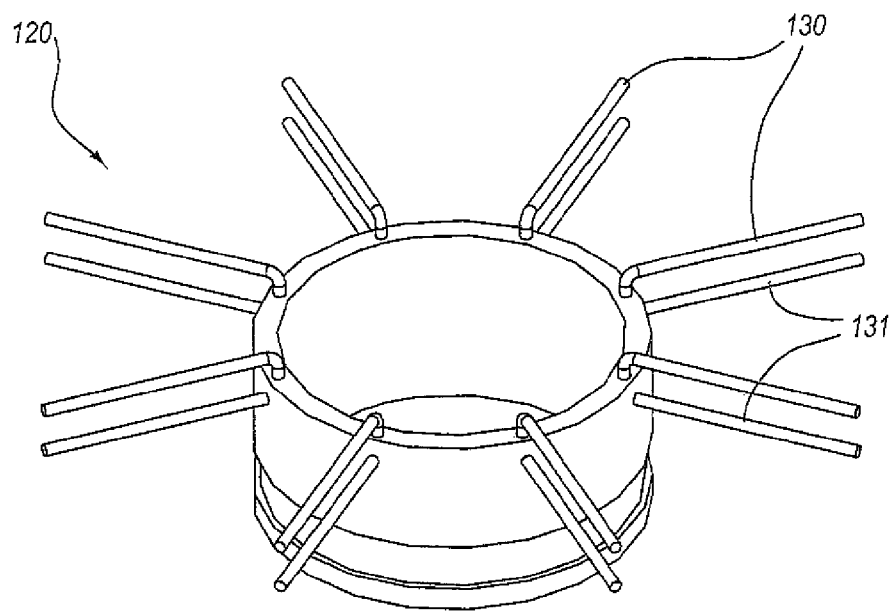
FIG. 11 is a perspective view of the connector illustrated in FIG. 10 with additional expandable members.
Figures 12, 13:
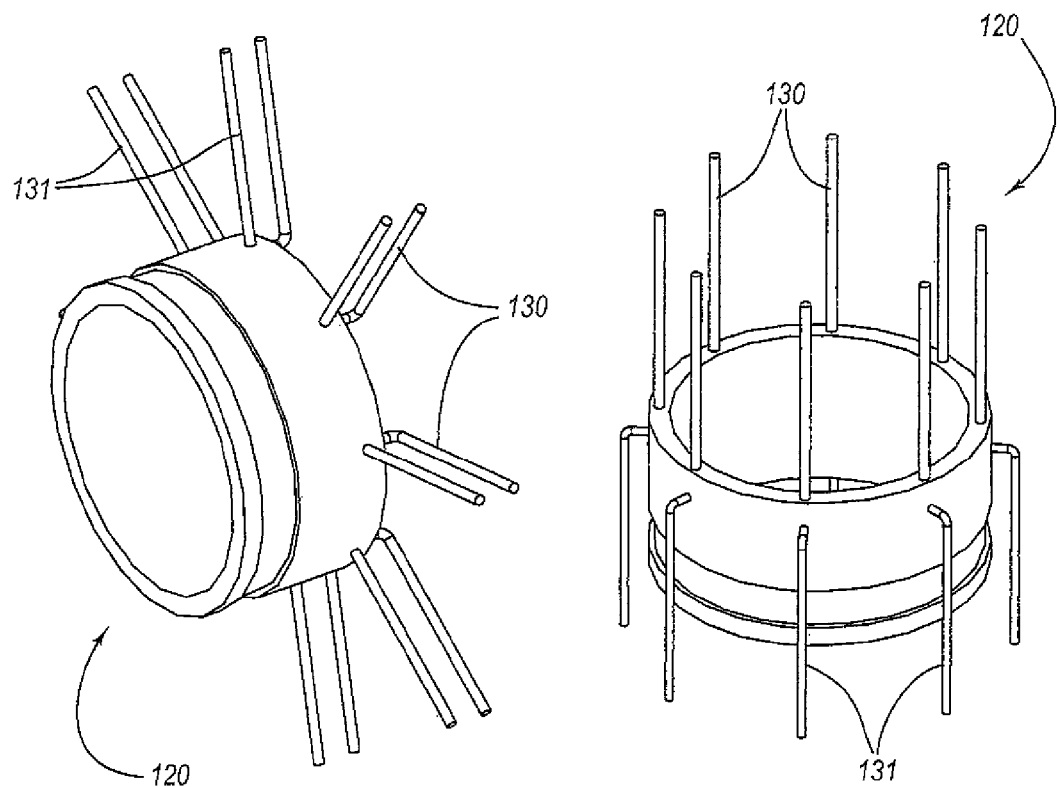
FIG. 12 is another perspective view of the connector illustrate in FIG. 11.
FIG. 13 is a perspective view of the connector illustrated in FIG. 12 in a deployed configuration.

FIGS. 11-13 illustrate alternative embodiments of connector 120. FIGS. 11-13 show connector 120 with internal expandable members 130 and external expandable members 131. When connector 120 is attached to a cardiovascular organ, internal expandable members 130 may deploy inside the cardiovascular organ, and external expandable members 131 may deploy outside the cardiovascular organ. FIGS. 11 and 12 show expandable members 130 and 131 in a deployed configuration, and FIG. 13 shows expandable members 130 and 131 in a delivery configuration.

Figure 14:
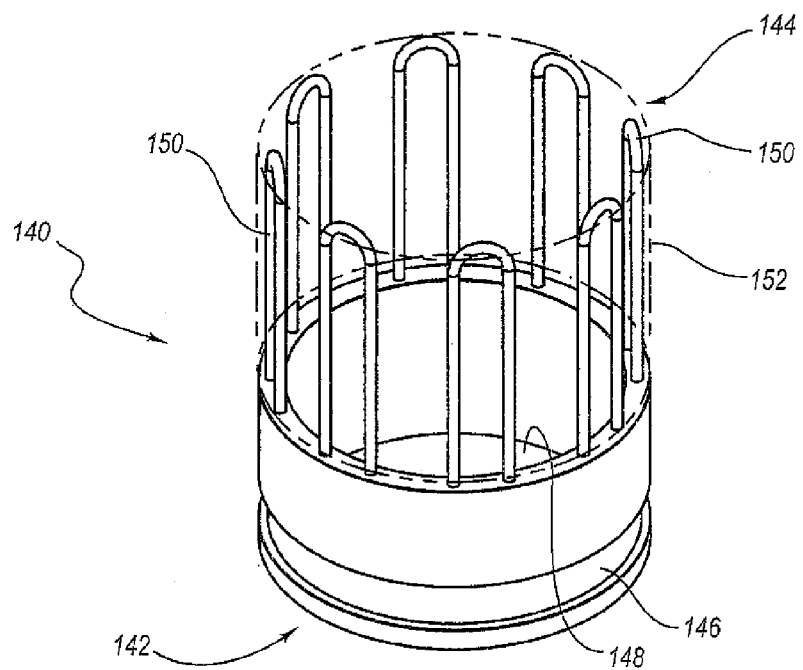
FIG. 14 is a perspective view of an exemplary connector according to certain embodiments.
Figure 15:
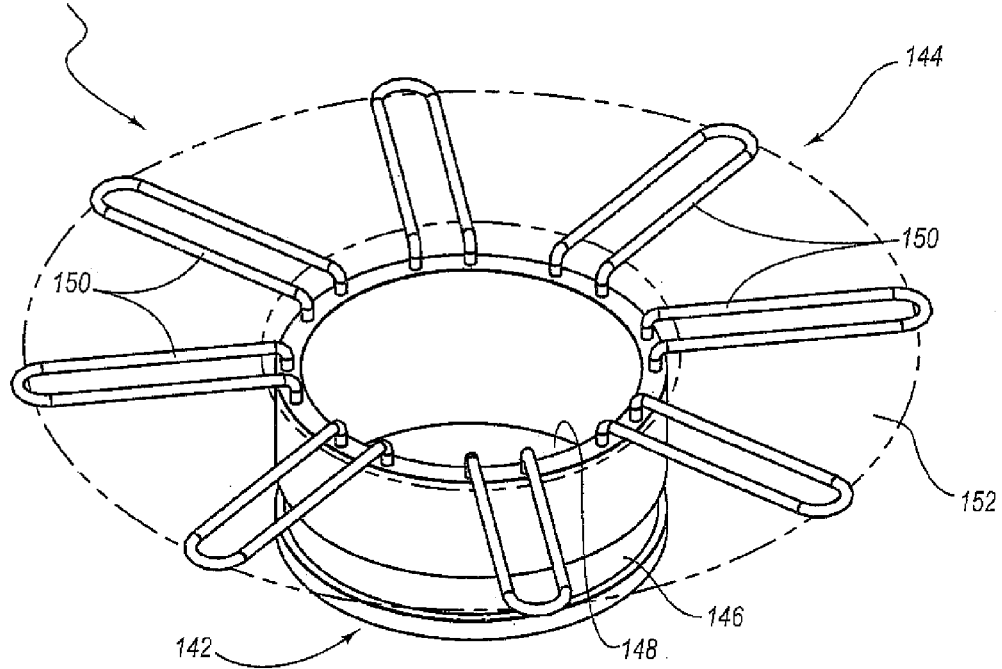
FIG. 15 is a perspective view of the connector illustrated in FIG. 14 in a deployed configuration.
Figure 16:
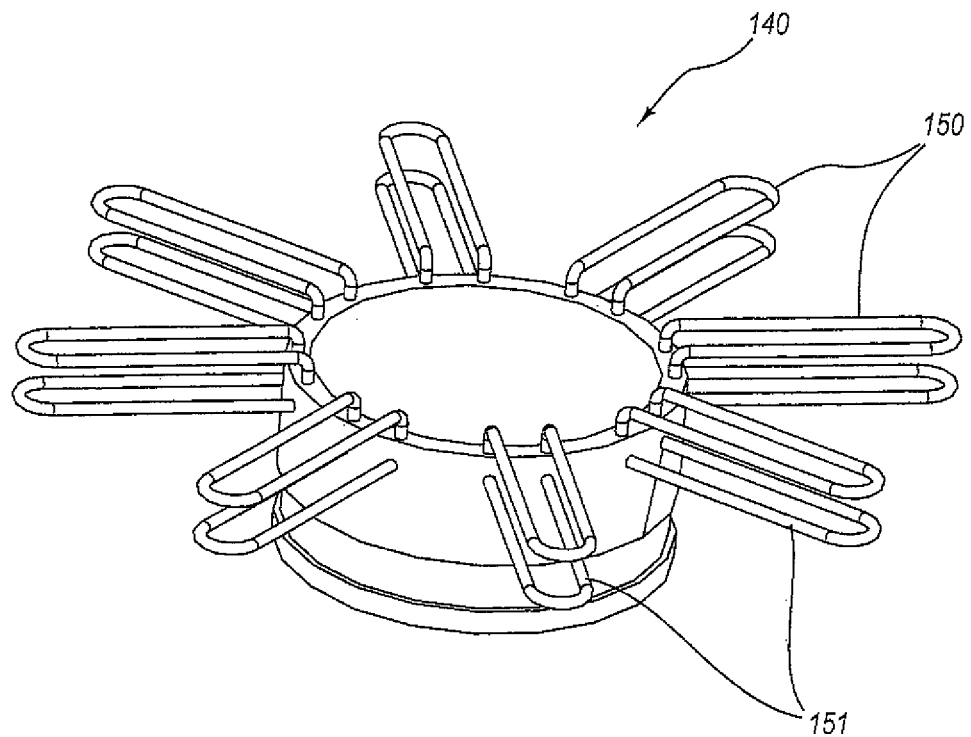
FIG. 16 is a perspective view of the connector illustrated in FIG. 15 with additional expandable members.
Figure 17:
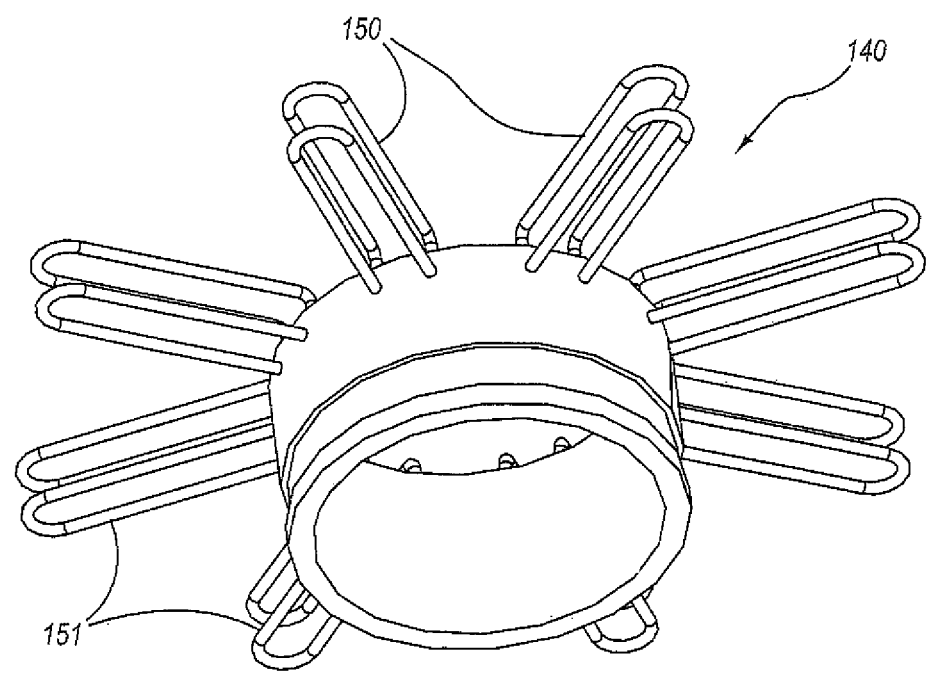
FIG. 17 is another perspective view of the connector illustrated in FIG. 16.

FIGS. 14 and 15 show a connector 140 that includes a distal end 142, a proximal end 144, and an opening 148. Distal end 142 may include a groove 146 for connection to a conduit. Proximal end 144 may include expandable members 150. FIG. 14 shows expandable members 150 in a delivery position, and FIG. 15 shows expandable members 150 in a deployed position. As shown in FIGS. 14 and 15, expandable members 150 may be loops. Expandable members 150 may comprise shape-memory material and may be formed as wire or tube. The design of connector 140 may be referred to as a flower design.

FIGS. 14 and 15 show that a fabric 152 may be sutured or otherwise connected to expandable members 150. Fabric 152 may help provide a seal between connector 140 and an opening in a cardiovascular organ. Fabric 152 may also help provide a stronger, more secure connection between connector 140 and a cardiovascular organ. Fabric, such as fabric 152, may be used with any of the other expandable members disclosed herein.

FIGS. 16-21 illustrate alternative embodiments of connector 140. FIGS. 16-21 show connector 140 with internal expandable members 150 and external expandable members 151. When a physician attaches connector 140 to a cardiovascular organ, internal expandable members 150 may deploy inside the cardiovascular organ, and external expandable members 151 may deploy outside the cardiovascular organ. FIGS. 16-21 show expandable members 150 and 151 in a deployed configuration.

Figure 18:
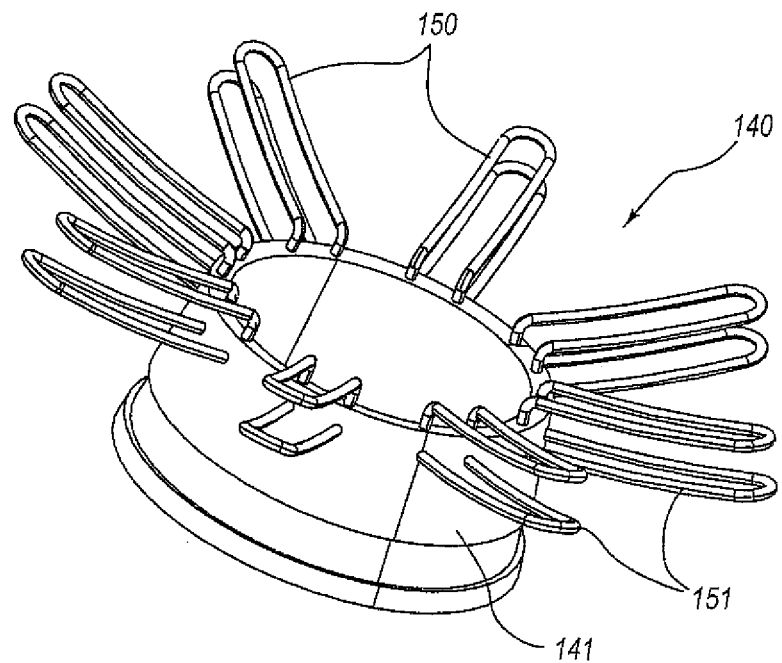
FIG. 18 is a perspective view of another configuration of the connector illustrated in FIG. 17.
Figure 19:
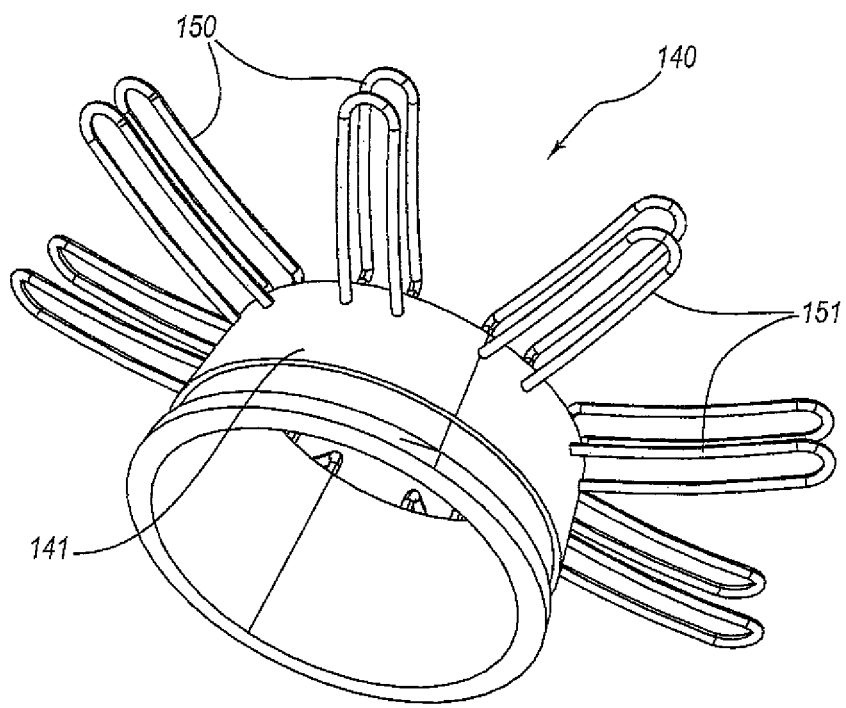
FIG. 19 is another perspective view of the connector illustrated in FIG. 18.
Figure 20:
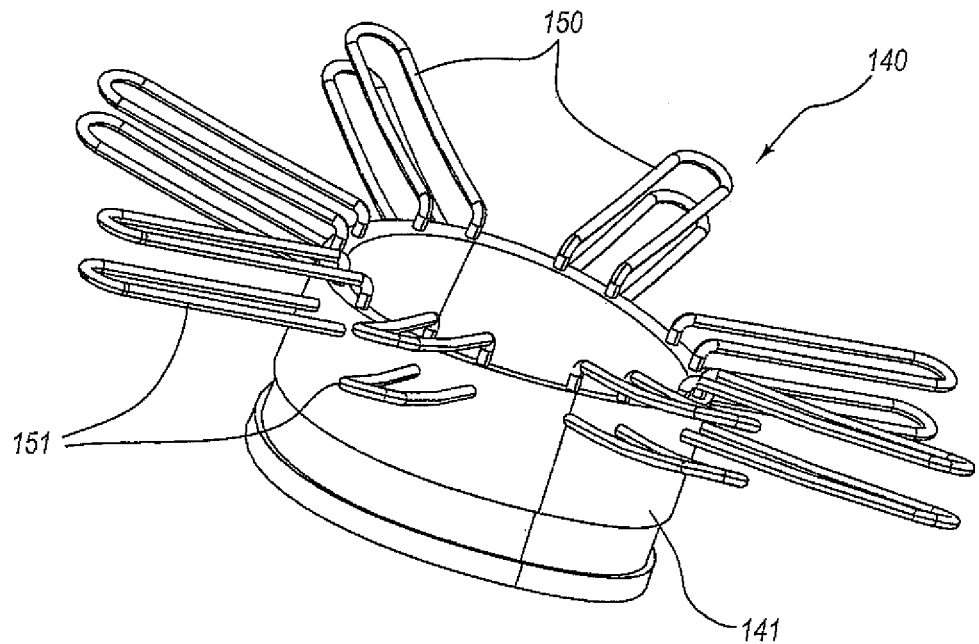
FIG. 20 is a perspective view of another configuration of the connector illustrated in FIG. 17.
Figure 21:
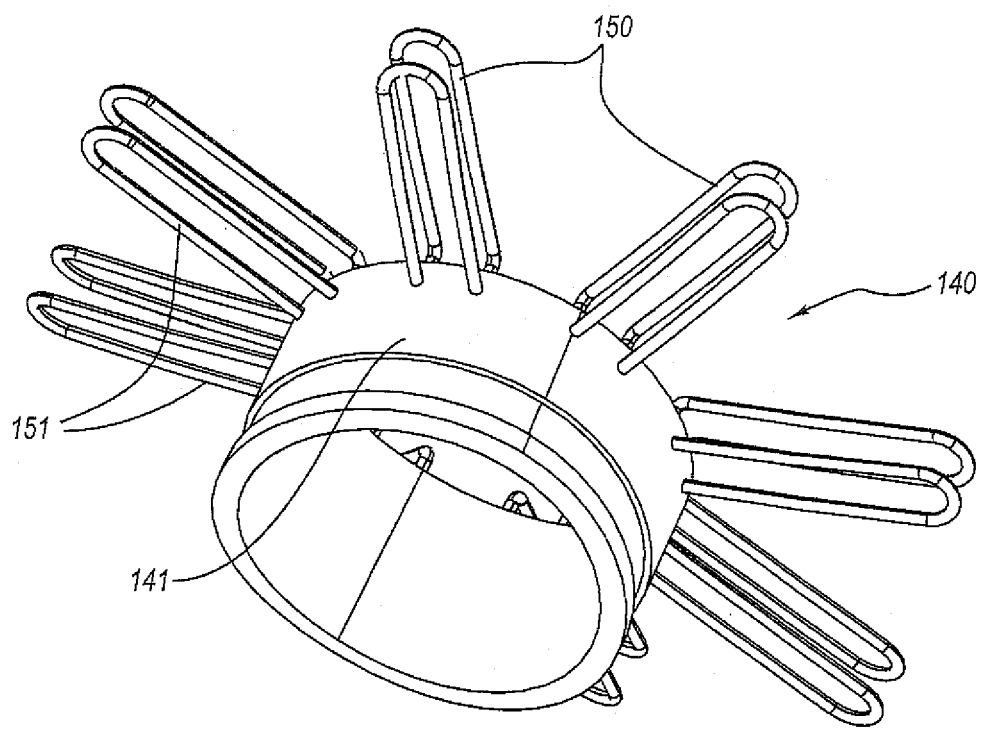
FIG. 21 is another perspective view of the connector illustrated in FIG. 20.

As shown in FIGS. 18 and 19, a body 141 of connector 140 may have a truncated conical shape. The shape of body 141 in FIGS. 18 and 19 may help connector 140 better conform to a heart apex anatomy. Body 141 of connector 140 may also have any other suitable shape. For example, FIGS. 20 and 21 show that body 141 of connector 140 may be in a curved shape to conform to an outside surface of a blood vessel. A connector that is curved to conform to the shape of a blood vessel may help improve the seal between the connector and the blood vessel. Any of the connectors disclosed herein may have bodies with the shapes illustrated in FIGS. 18-21. Any of the connectors disclosed herein may also have any other suitable shape.

Figure 22:
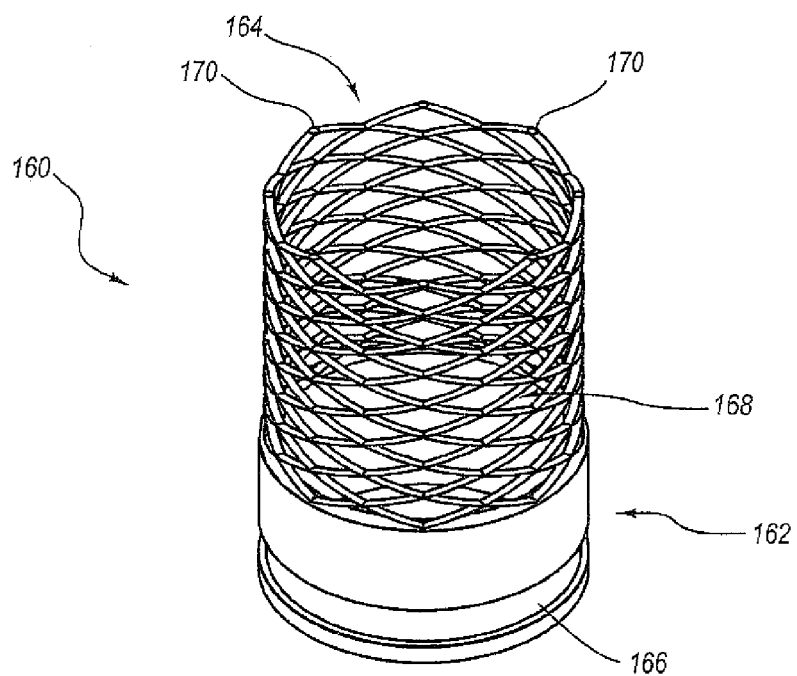
FIG. 22 is a perspective view of an exemplary connector according to certain embodiments.
Figure 23:
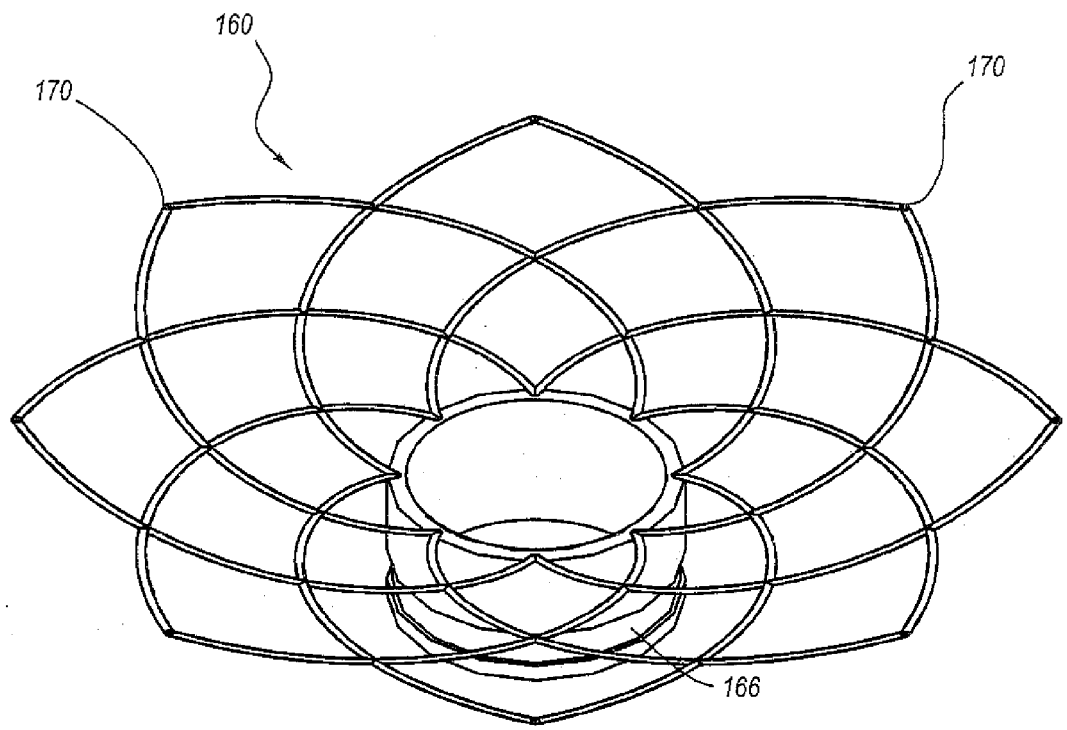
FIG. 23 is a perspective view of the connector illustrated in FIG. 22 in a deployed configuration.
Figure 24:
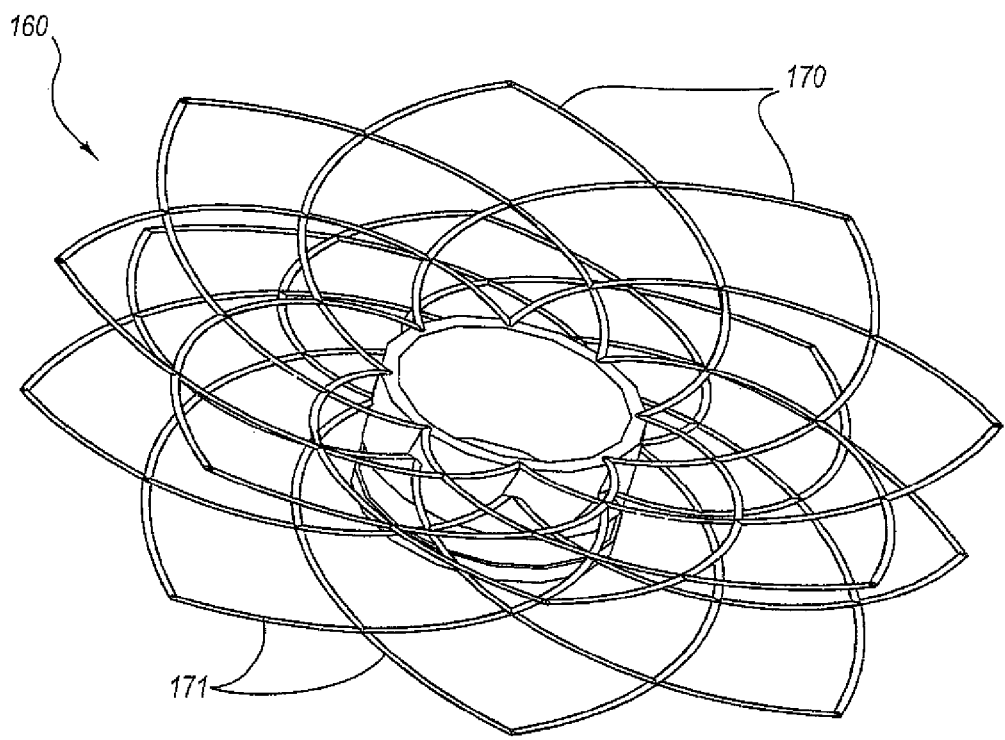
FIG. 24 is a perspective view of the connector illustrated in FIG. 23 with additional expandable members.
Figure 25:
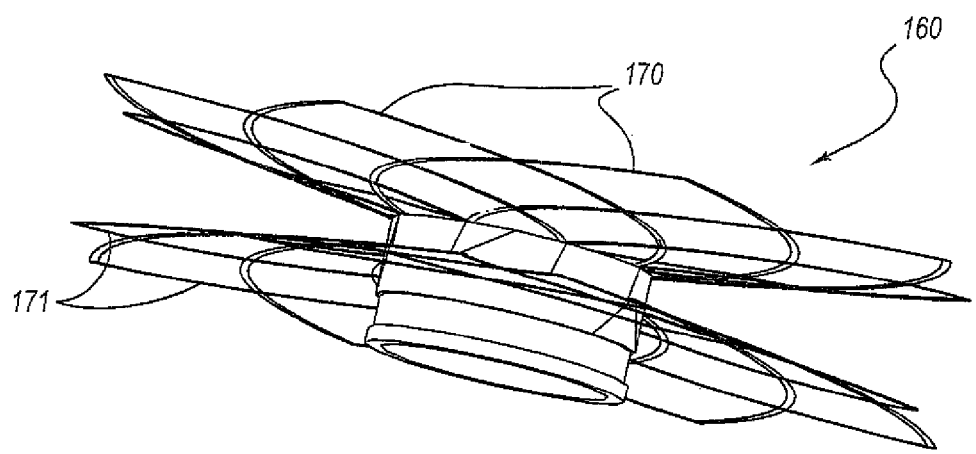
FIG. 25 is another perspective view of the connector illustrated in FIG. 24.

FIGS. 22 and 23 show a connector 160 that includes a distal end 162, a proximal end 164, and an opening 168. Distal end 162 may include a groove 166 for connection to a conduit. Proximal end 164 may include expandable members 170. FIG. 22 shows expandable members 170 in a delivery position, and FIG. 23 shows expandable members 170 in a deployed position. As shown in FIG. 23, expandable members 170 may be loops that are shaped like leaves or flower petals. Expandable members 170 may overlap each other, which may provide additional rigidity and torque resistance when connector 160 is in a deployed configuration. The overlapped configuration of expandable members 170 may be referred to as a weave design. FIGS. 24 and 25 illustrate connector 160 with internal expandable members 170 and external expandable members 171. Both FIGS. 24 and 25 show expandable members 170 and 171 in a deployed configuration.

Figure 26:
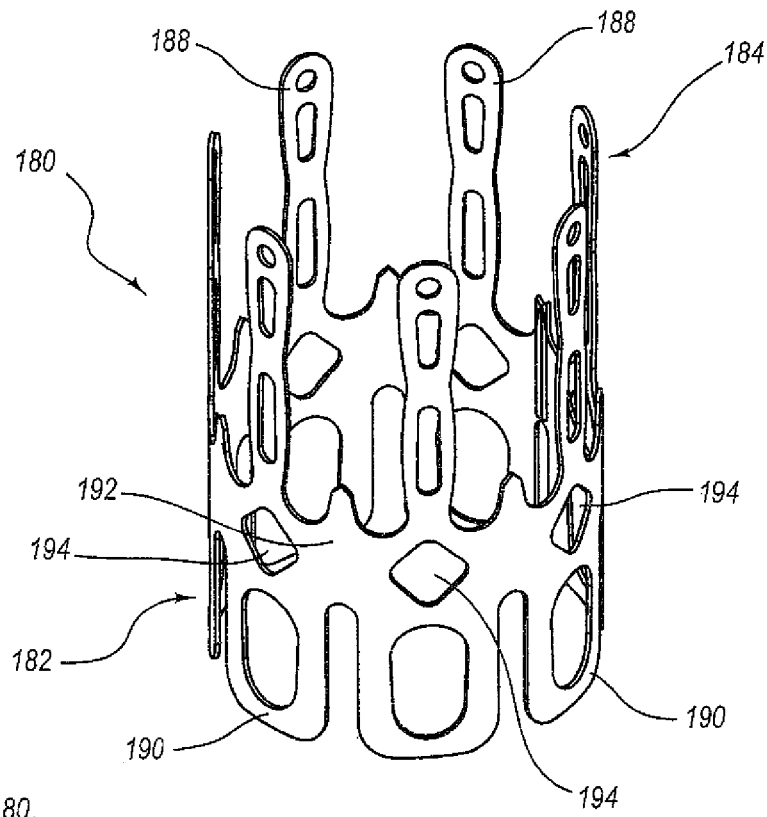
FIG. 26 is a perspective view of an exemplary connector according to certain embodiments.
Figure 27:
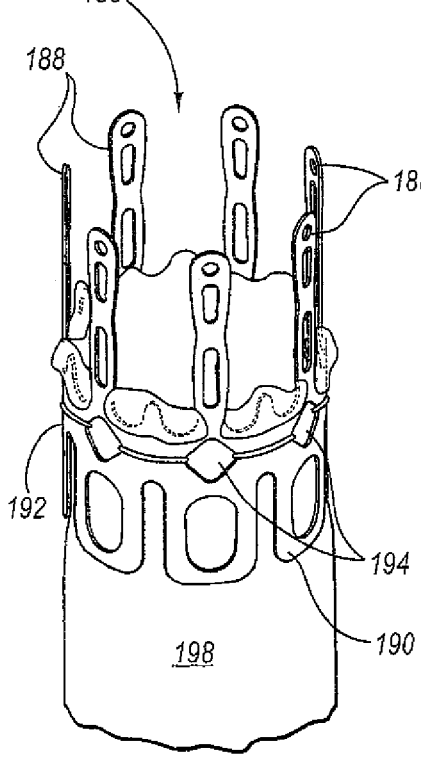
FIG. 27 is a perspective view of an exemplary conduit sutured to the connector illustrated in FIG. 26.
Figure 28:
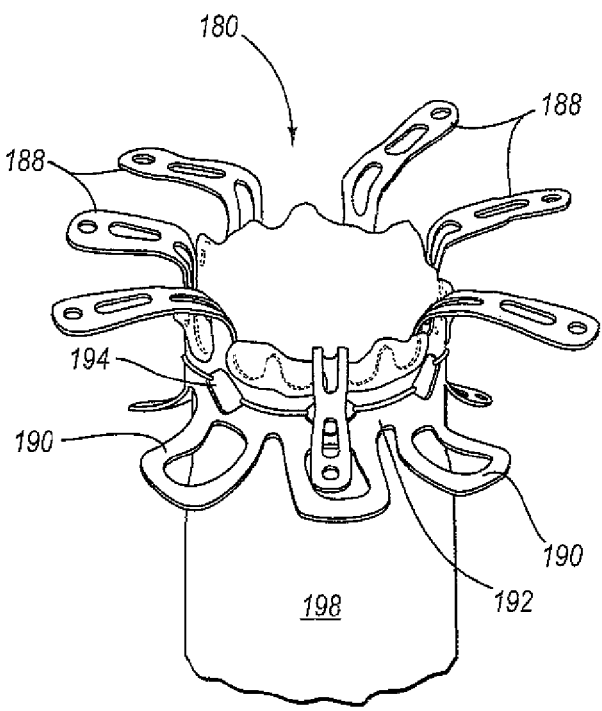
FIG. 28 is a perspective view of the connector illustrated in FIG. 26 in a deployed configuration.

FIGS. 26-28 illustrate a connector 180 with a distal end 182 and a proximal end 184. FIGS. 26 and 27 show connector 180 in a delivery configuration, and FIG. 28 shows connector 180 in a deployed configuration. A middle portion 192 of connector 180 may include openings 194 that allow connector 180 to be sutured to a conduit 198, as shown in FIGS. 27 and 28. Proximal end 184 may include expandable members 188, and distal end 182 may include expandable members 190. As shown in FIG. 28, expandable members 190 and 188 may expand to form a clamp capable of securing connector 180 to a cardiovascular organ wall. The design of connector 180 may be referred to as a clamping design.

Figure 29:
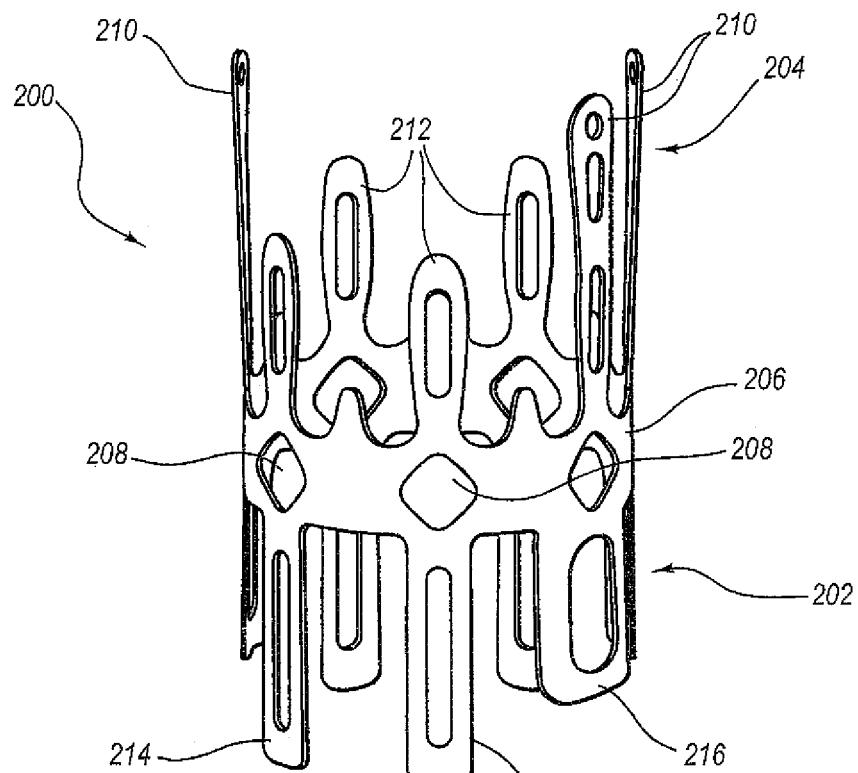
FIG. 29 is a perspective view of an exemplary connector according to certain embodiments.

FIG. 29 shows a connector 200 in a delivery configuration. Connector 200, like connector 180, may be referred to as a clamping design. A distal end 202 of connector 200 may include expandable members 214 and 216. As shown, expandable members 214 may be longer than expandable members 216. A proximal end 204 of connector 200 may include expandable members 210 and 212, and expandable members 212 may be shorter than expandable members 210. Expandable members 210, 212, 214, and 216 may deploy to clamp to a wall of a cardiovascular organ.

Figure 30:
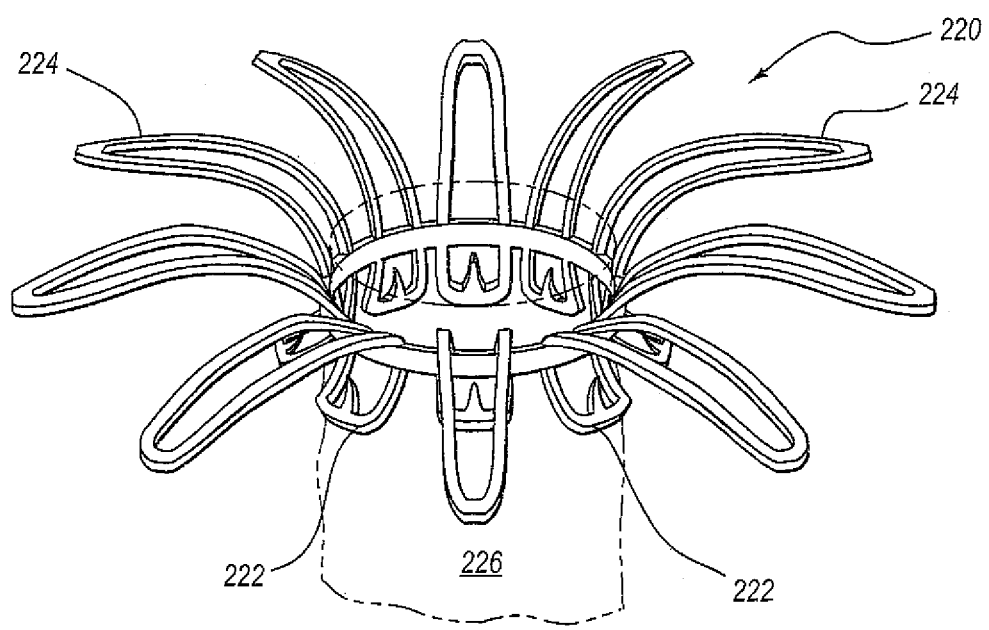
FIG. 30 is a perspective view of an exemplary connector according to certain embodiments.

FIG. 30 illustrates a connector 220 in a deployed configuration. Connector 220 may be attached to a conduit 226. Connector 220 has a clamping design similar to connectors 180 and 200. Connector 220 includes expandable members 222 and expandable members 224. Expandable members 224 may be longer than expandable members 222. In other embodiments, expandable members 222 may be longer than expandable members 224. As shown, expandable members 222 and 224 may oppose each other such that they are capable of clamping to an opening in a cardiovascular organ.

Figure 31:
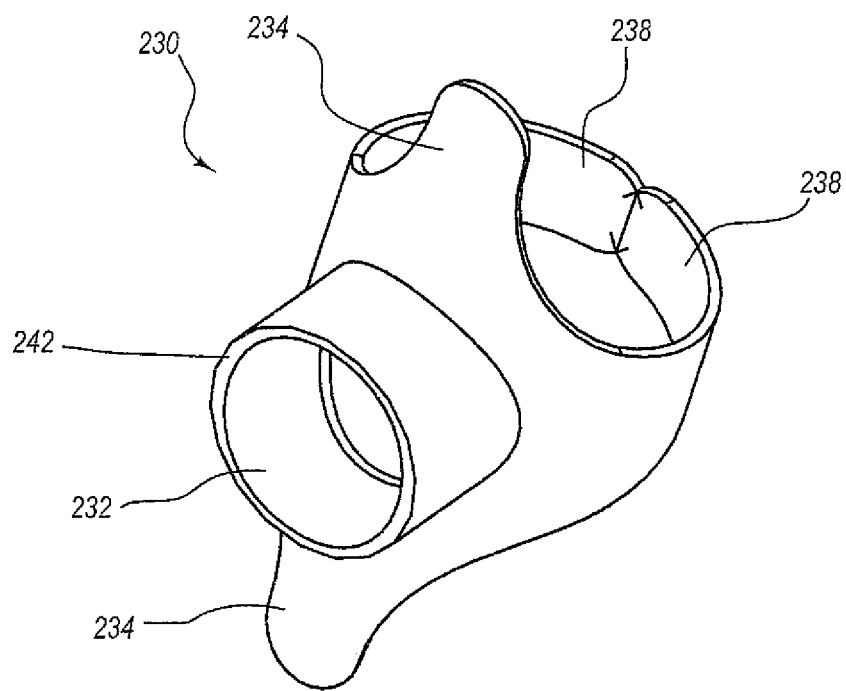
FIG. 31 is a perspective view of an exemplary internal connector section according to certain embodiments.
Figure 32:
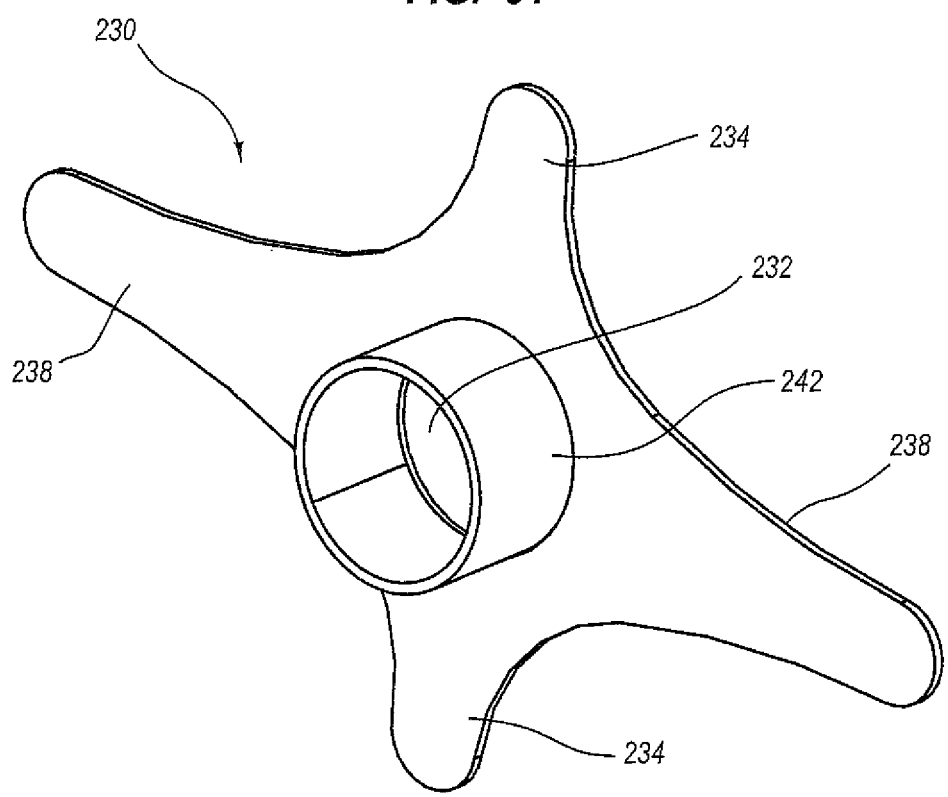
FIG. 32 is a perspective view of the connector section illustrated in FIG. 31 in a deployed configuration.
Figure 33:
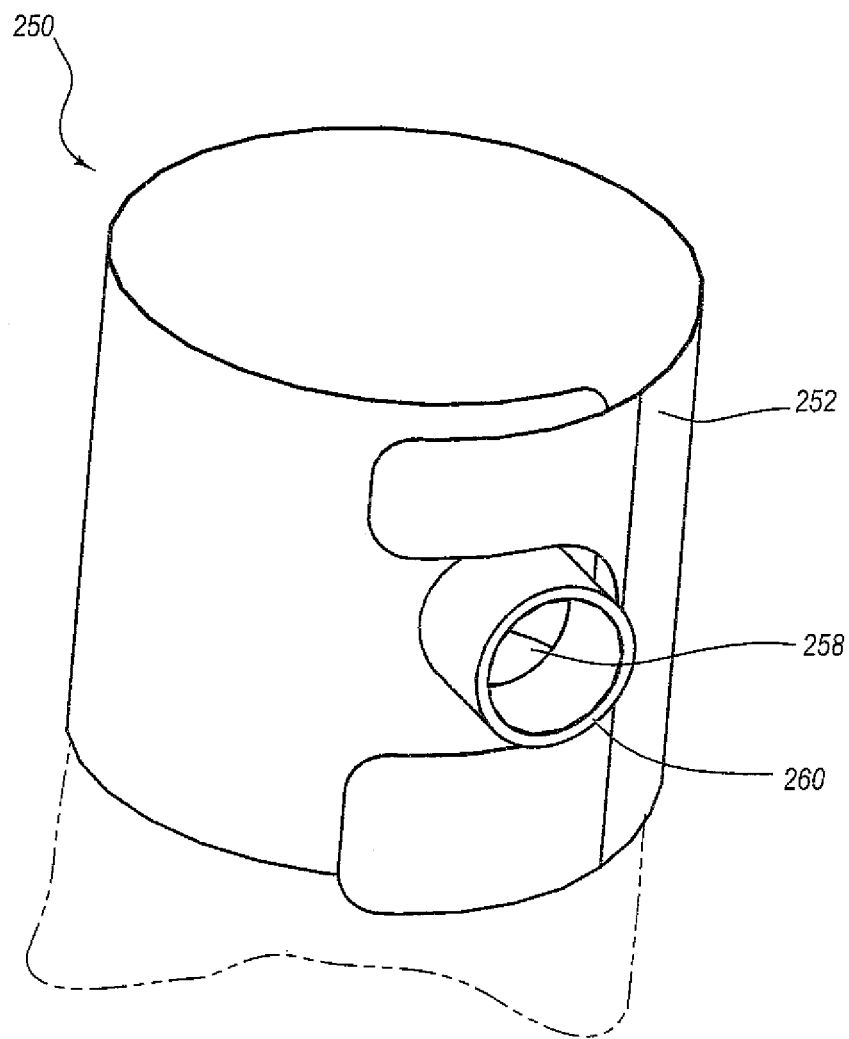
FIG. 33 is a perspective view of an exemplary external connector section according to certain embodiments.

FIGS. 31-33 illustrate a two-part cardiovascular conduit system connector. FIGS. 31 and 32 show an internal connector section 230, and FIG. 33 shows an external connector section 250. Connector section 230, which may be configured to secure to an inside of a cardiovascular organ, includes arms 234, expandable members 238, and a cylinder 242. Cylinder 242 may include an opening 232. FIG. 31 shows connector section 230 in a cylindrical delivery configuration. After connector section 230 is delivered to the inside of a cardiovascular organ, connector section 230 may deploy by extending expandable members 238, as shown in FIG. 32.

FIG. 33 illustrates connector section 250 with an expandable member 252. Connector section 250 may also include a cylinder 260 with an opening 258. Connector section 250 may be designed to secure to the outside of the cardiovascular organ. Connector section 250 may be coupled to connector section 230 after connector section 230 is deployed inside the cardiovascular organ. Cylinder 242 of connector section 230 may be attached to cylinder 260 of connector section 250. Expandable member 252 of connector section 250 may be deployed before or after connector section 250 is attached to connector section 230. According to some embodiments, connector section 250 may be used as an external attachment with other embodiments of connectors disclosed herein. Using a two-part connector may provide additional support for the cardiovascular organ and help prevent aneurisms at the connection site.

FIGS. 34 and 35 show an expandable connector 280. Connector 280 may be attached to or integrally incorporated into a conduit 270. Conduit 270 may be made of any suitable material. For example, conduit 270 may be made of a thermoplastic polymer resin such as polyethylene terephthalate (e.g., DACRON). The expandable section of connector 280 may also be referred to as an expandable member.

Connector 280 may be an expandable stent designed to expand when placed in an opening of a cardiovascular organ. Connector 280 may be deployable from a delivery configuration, as shown in FIG. 34, to a deployed configuration, as shown in FIG. 35. In a delivery configuration, connector 280 may be cylindrical, conical, or any other suitable shape. In a deployed position, connector 280 may apply a radial force to the opening in the cardiovascular organ. The radial force applied by connector 280 may secure connector 280 to the cardiovascular organ and provide an improved seal with the opening in the cardiovascular organ. Connector 280 may also include hooks 282, which may help secure connector 280 to the cardiovascular organ.

FIG. 36 shows connector 280 connected to a left ventricle 294 of a heart 290. After a surgeon cores opening 291 in a wall 292 of heart 290, connector 280 may be inserted into opening 291. A retaining member, such as a sheath, may be retracted from connector 280 to allow connector 280 to expand and apply a radial force to opening 291. The retaining member may also hold hooks 282 in a delivery configuration, and when the retaining member is retracted, hooks 282 may deploy to secure connector 280 to the inside of left ventricle 294. Connector 280 may include an opening that allows blood to flow between left ventricle 294 and conduit 270. Connector 280 may also include hooks 284 that attach to an outside of left ventricle 294, as shown in FIGS. 37 and 38.

FIGS. 39 and 40 illustrate a connector 300 that may be integrally incorporated into or attached to conduit 270. FIG. 39 shows connector 300 in a delivery configuration, and FIG. 40 illustrates connector 300 in a deployed configuration. Connector 300 may be a stent rolled to a small diameter in the delivery position, and connector 300 may expand to a larger diameter in a deployed position. Connector 300, in a deployed position, may apply radial force to an opening in a cardiovascular organ.

Figure 43:
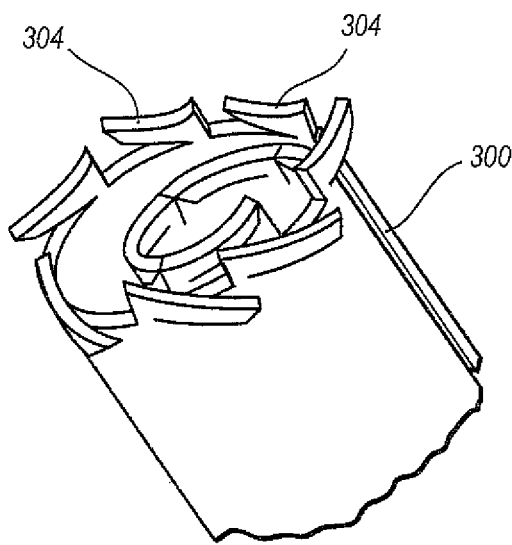
FIG. 43 is a perspective view of an exemplary expandable connector according to certain embodiments.
Figure 44:
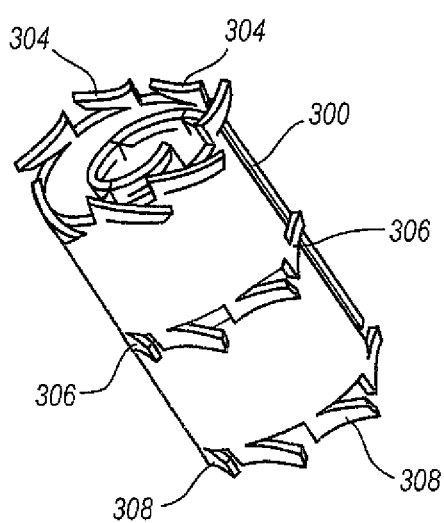
FIG. 44 is a perspective view of an exemplary expandable connector according to certain embodiments.
Figure 45:
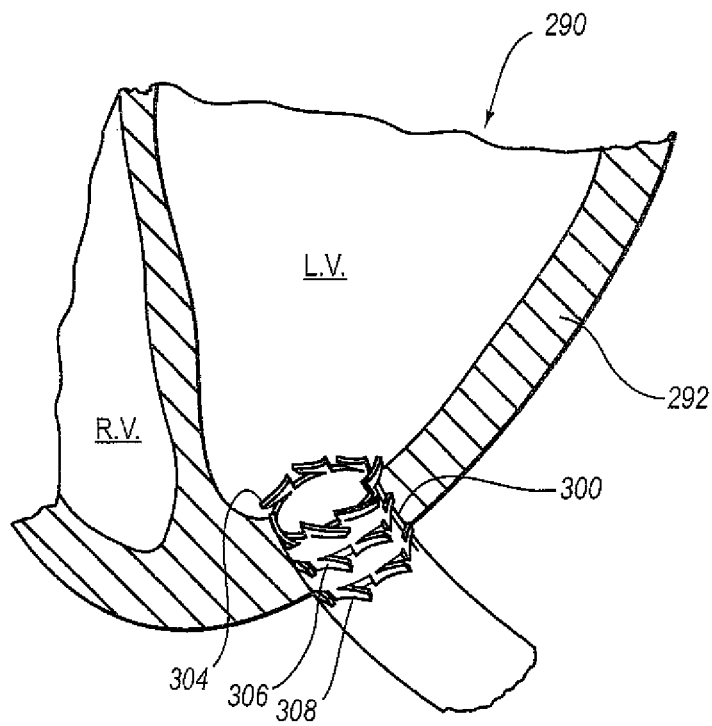
FIG. 45 is a cross-sectional view of a portion of a heart with the expandable connector illustrated in FIG. 44 attached to the heart.

As shown in FIGS. 41 and 42, connector 300 may include barbs 302. In a deployed position, barbs 302 may attach connector 300 to left ventricle 294 of heart 290, as shown in FIG. 42. FIG. 43 shows that a proximal end of connector 300 may include hooks 304. In some embodiments, as shown in FIG. 44, a middle section of connector 300 may include hooks 306, and a distal end of connector 300 may include hooks 308. FIG. 45 shows that hooks 304, 306, and 308 may press into wall 292 of heart 290 as connector 300 deploys. When deployed, hooks 304, 306, and 308 may provide a secure attachment to the heart 290.

Figure 46:
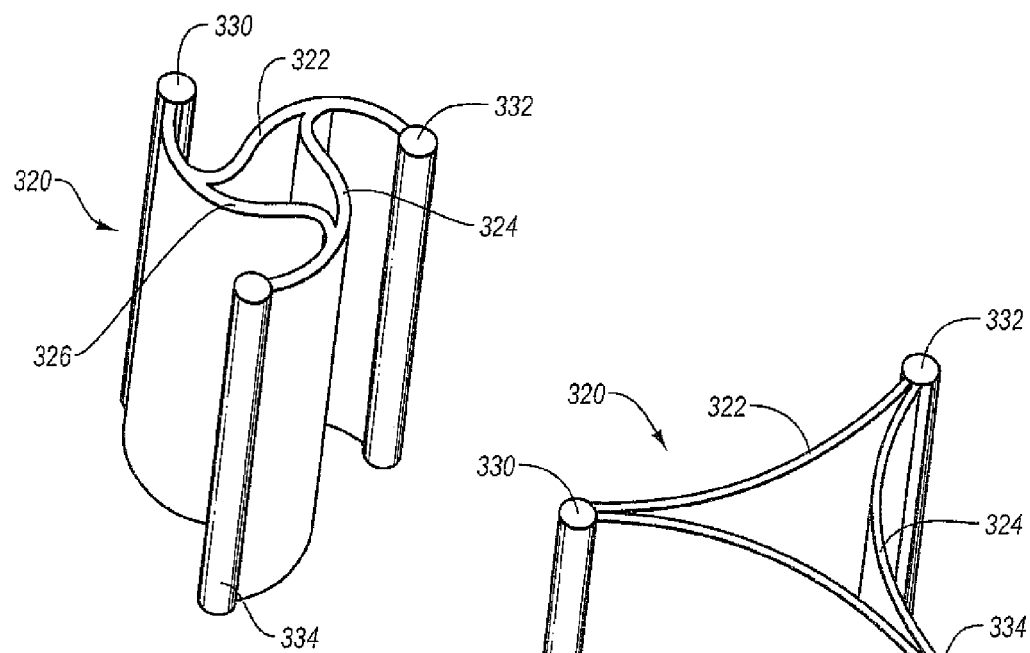
FIG. 46 is a perspective view of an exemplary expandable connector according to certain embodiments.
Figure 47:
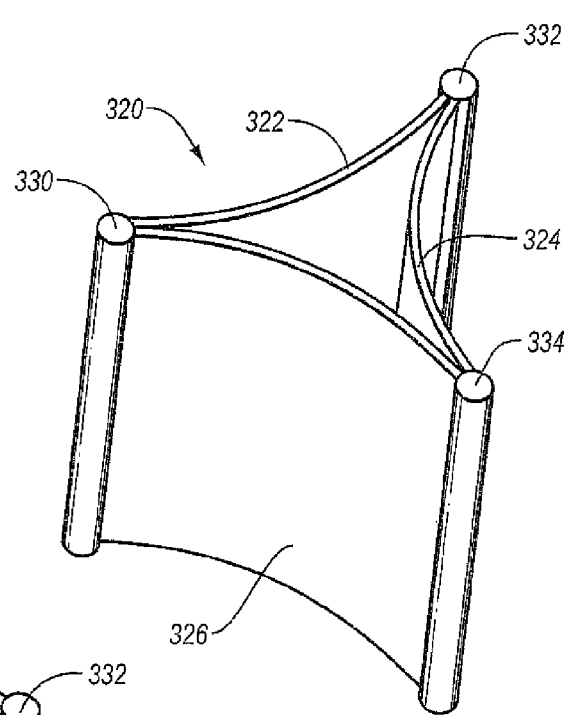
FIG. 47 is a perspective view of the connector illustrated in FIG. 46 as it begins to expand.
Figure 48:
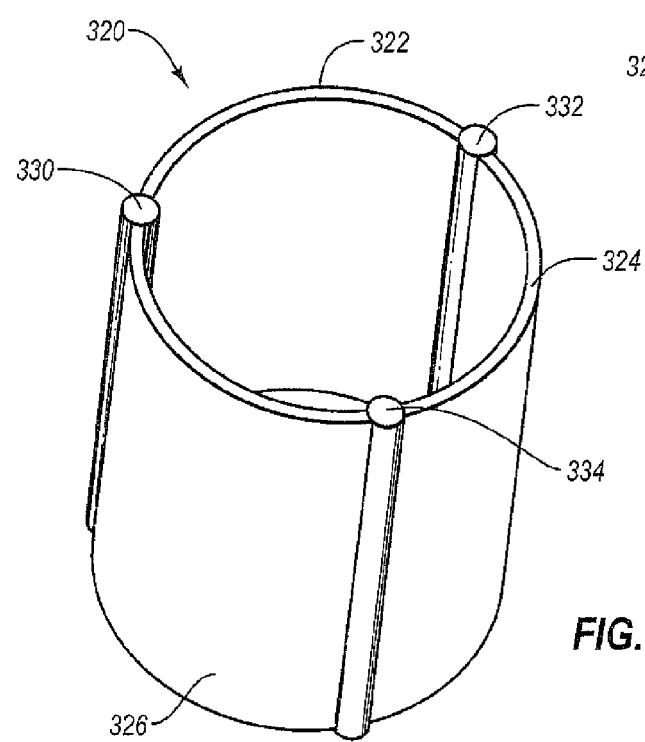
FIG. 48 is a perspective view of the connector illustrated in FIG. 48 in a deployed configuration.

FIGS. 46-48 illustrate a three-section connector 320. Connector 320 may include sections 322, 324, and 326. Sections 322, 324, and 326 may be made of a flexible material capable of rolling up or collapsing in the delivery configuration shown in FIG. 46. Connector 320 may also include a hinge 330 that connects section 322 to section 326, a hinge 332 that connects section 324 to section 322, and a hinge 334 that connects section 324 to section 326. Any other suitable attachment mechanism may be used to connect sections 322, 324, and 326. Also, connector 320 may include any suitable number of sections and/or hinges.

After connector 320 is inserted into an opening in a cardiovascular organ, connector 320 may be deployed. FIG. 47 shows connector 320 as it begins to deploy. In the first stage of deployment, connector 320 may unroll from the configuration shown in FIG. 46 to the configuration shown in FIG. 47. Next, sections 322, 324, and 326 of connector 320 may expand from the positions illustrated in FIG. 47 to the positions illustrated in FIG. 48. Connector 320 may be referred to as an expandable member and/or expandable connector.

Figure 49:
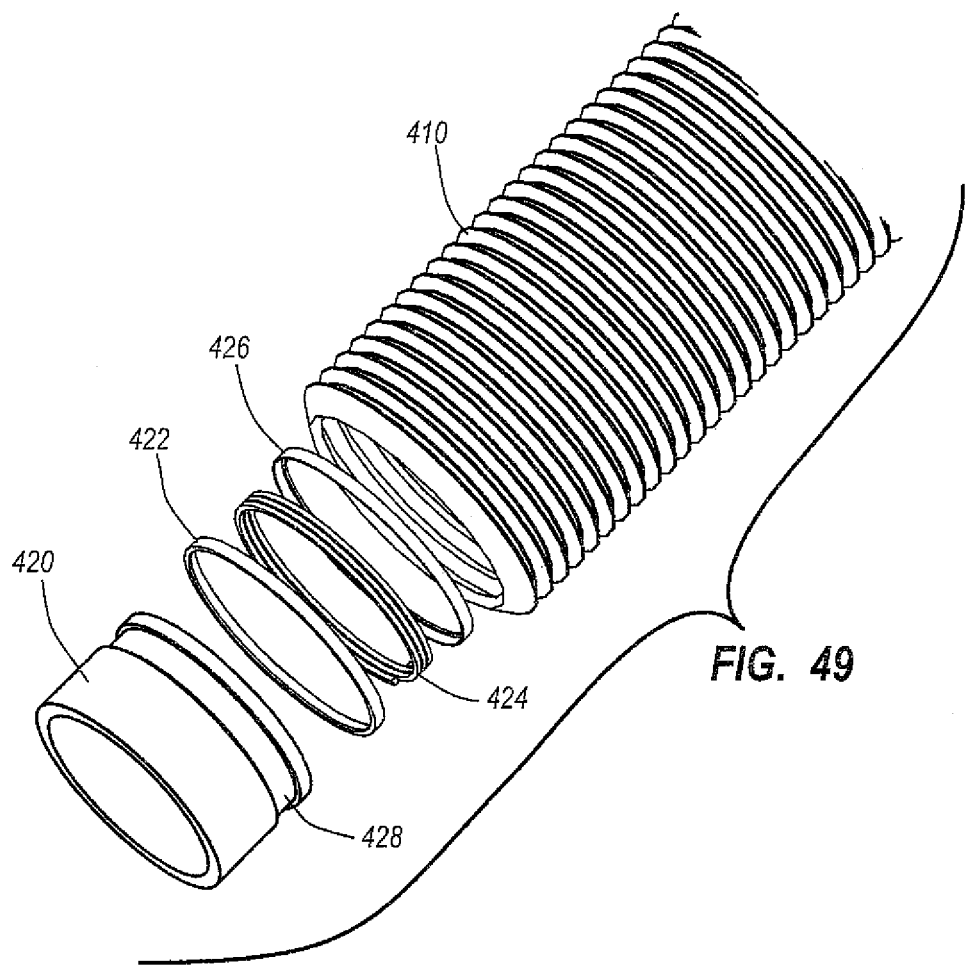
FIG. 49 is a perspective view of an exemplary connector-conduit assembly according to certain embodiments.

FIGS. 49-53 illustrate how connectors may be rotatably attached to a conduit. FIG. 49 shows a connector 420 and a conduit 410. Connector 420 may be rotatably attached to conduit 410 by placing spring 424 and rings 422 and 426 over conduit 410 and within groove 428 of connector 420.

Figure 50:
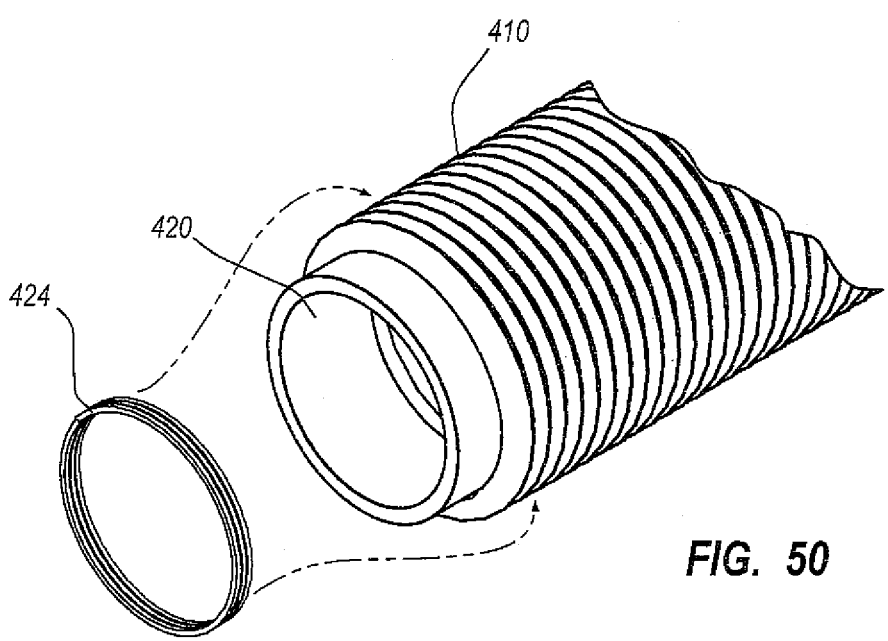
FIG. 50 is a perspective view of the conduit illustrated in FIG. 49 placed over the connector illustrated in FIG. 49.
Figure 51:
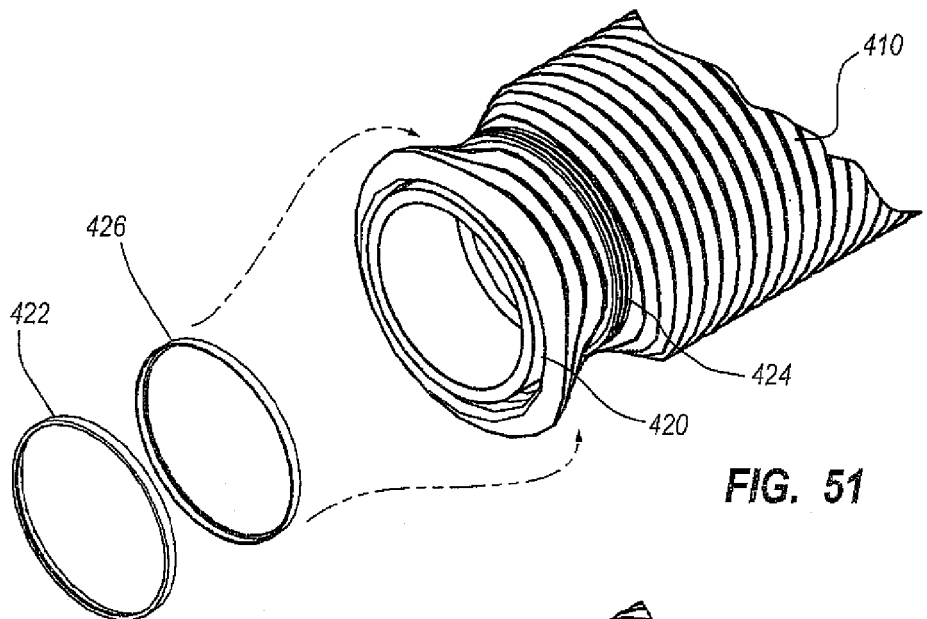
FIG. 51 is a perspective view of a spring attaching the conduit illustrated in FIG. 50 to the connector illustrated in FIG. 50.
Figure 52:
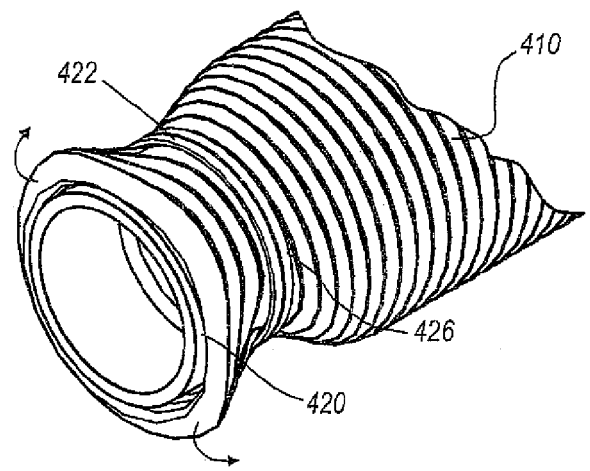
FIG. 52 is a perspective view of rings placed over the spring illustrated in FIG. 51.
Figure 53:
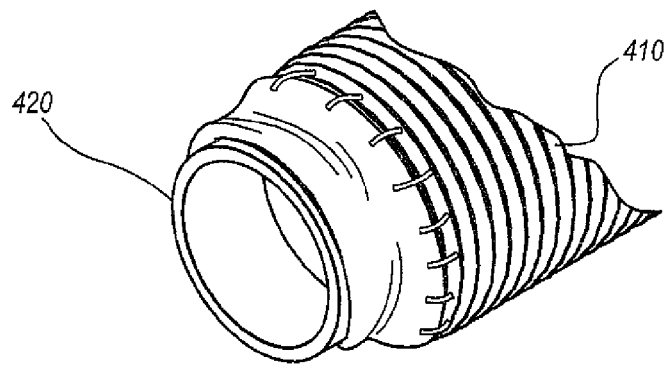
FIG. 53 is a perspective view of the conduit-connector assembly illustrated in FIG. 52.

A first step of connecting conduit 410 to connector 420 may include sliding conduit 410 over the grooved end of connector 420, as shown in FIG. 50. Spring 424 may then be placed around conduit 410 and seated in groove 428 of connector 420, thereby rotatably securing conduit 410 to connector 420, as shown in FIG. 51. Next, rings 422 and 426 may be placed over spring 424 and seated in groove 428 to hold spring 424 in place, as shown in FIG. 52. A single ring, instead of two rings, may be positioned over spring 424. After rings 422 and 426 are positioned over spring 424, an end of conduit 410 may be folded back over rings 422 and 426 and spring 424. The end of conduit 410 may be sutured to a portion of conduit 410 on the other side of the ring-and-spring assembly to secure the ring-and-spring assembly in place, as shown in FIG. 53.

According to various embodiments, a conduit may be rotatably attached to a connector using any suitable attachment mechanism other than a ring-and-spring assembly. In some embodiments, the conduit may be sutured to the connector to provide a fixed connection between the conduit and the connector. Suture may also be wound around the conduit in a groove of a connector to attach the connector to the conduit.

Figure 54:
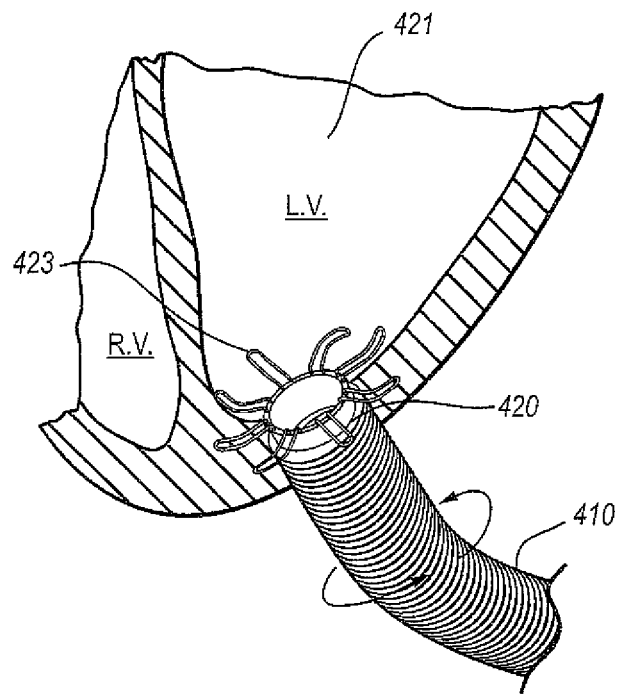
FIG. 54 is a perspective view of an exemplary cardiovascular conduit system mounted to a portion of a heart according to certain embodiments.
Figure 55:
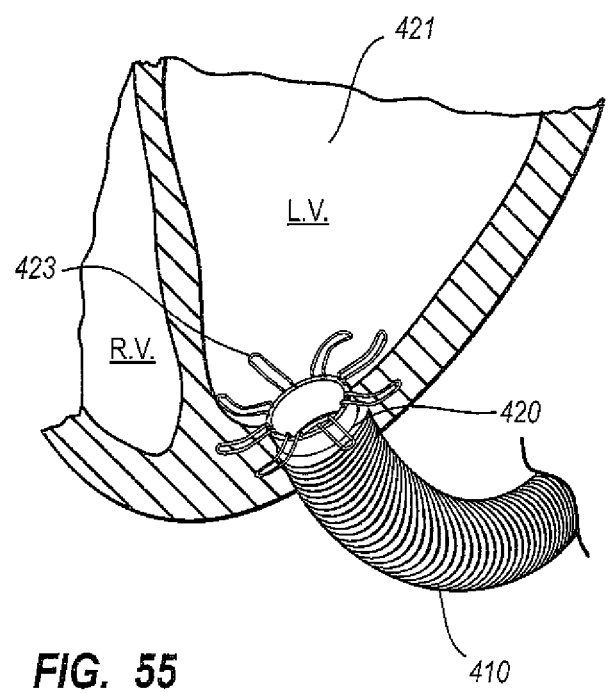
FIG. 55 is a perspective view of an exemplary cardiovascular conduit system mounted to a portion of a heart according to certain embodiments.

The procedure shown in FIGS. 49-53 may result in a conduit-connector attachment that allows the conduit to rotate relative to the connector. As shown in FIGS. 54 and 55, connector 420 may include expandable members 423. Expandable members 423 of connector 420 may deploy to attach conduit 410 to a left ventricle 421 of a heart. FIGS. 54 and 55 show that conduit 410 may rotate relative to connector 420. This additional flexibility may prevent kinking and damage to the conduit when a surgeon implants the conduit. The flexibility provided by a rotating conduit may also reduce the risk of gastrointestinal complications caused by the conduit pressing against other internal organs.

Figure 56:
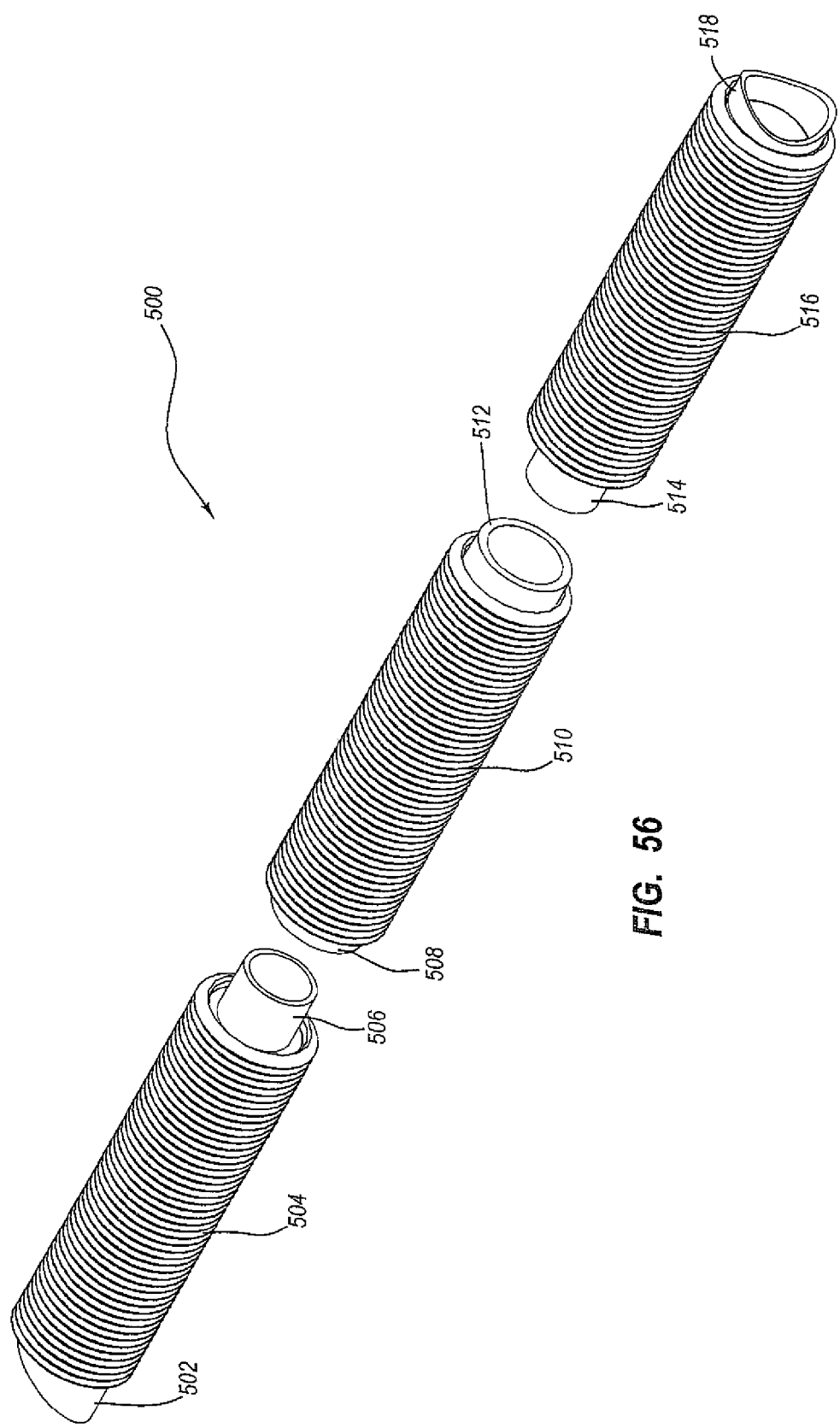
FIG. 56 is a perspective view of an exemplary cardiovascular conduit system according to certain embodiments.

FIG. 56 is a perspective view of a cardiovascular conduit system 500. An apical connector 502 (i.e., a connector designed to attach to an apex of a heart) may be attached to a first end of conduit 504. A second end of conduit 504 may be attached to a connector 506. Connector 506 may be dimensioned to snap or otherwise attach to another connector, such as connector 508. Connectors 508 and 512 may be attached to a conduit 510 to form a cardiovascular conduit extension. A cardiovascular conduit extension may be used to provide extra length and/or flexibility to a cardiovascular conduit system.

Connector 512 may be dimensioned to attach to a connector 514. Connector 514 may be attached to a first end of a conduit 516, and a connector 518 may be attached to a second end of conduit 516. Connector 518 may be an aortic connector (i.e., a connector designed to attach to an aorta or other blood vessel). Connector 518 and/or connector 502 may be any of the various connectors illustrated herein. Also, the connectors shown in FIG. 56 may be attached to the conduit shown in FIG. 56 using a ring-and-spring assembly.

Figure 57:
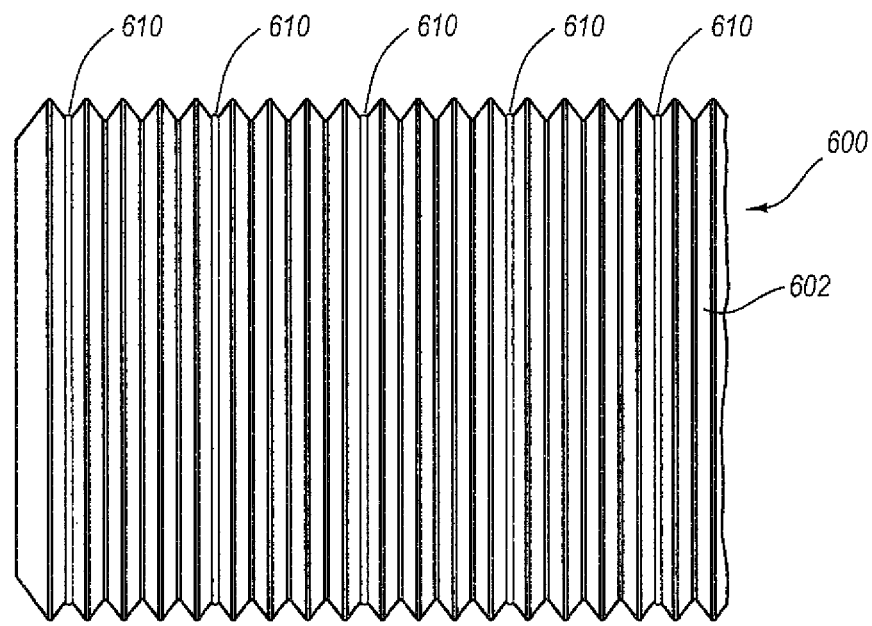
FIG. 57 is a side view of an exemplary reinforced conduit according to certain embodiments.
Figure 58:
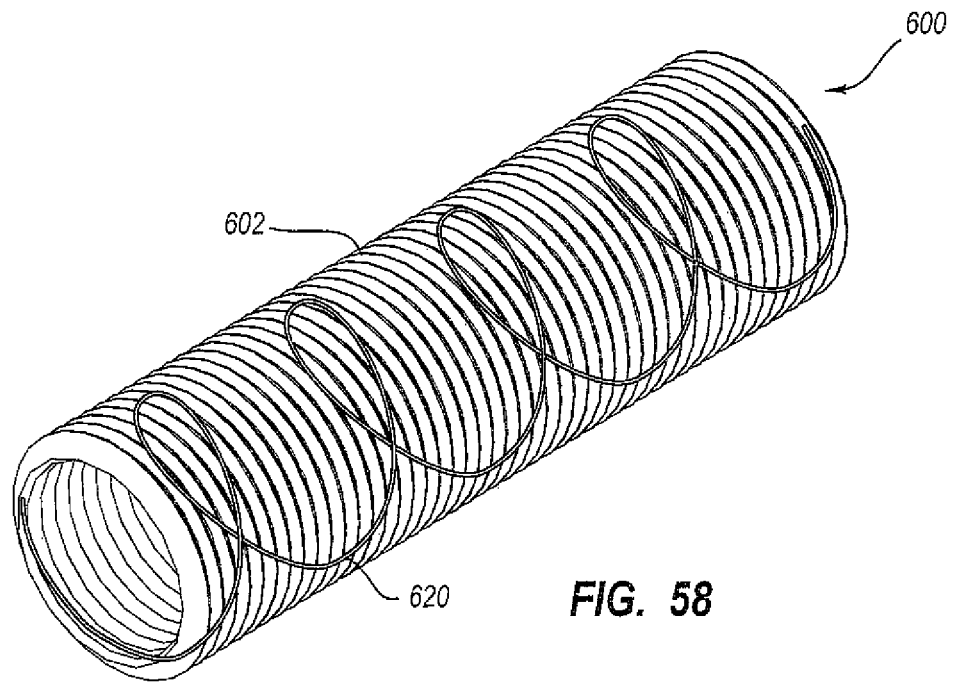
FIG. 58 is a perspective view of an exemplary reinforced conduit according to certain embodiments.
Figure 59:
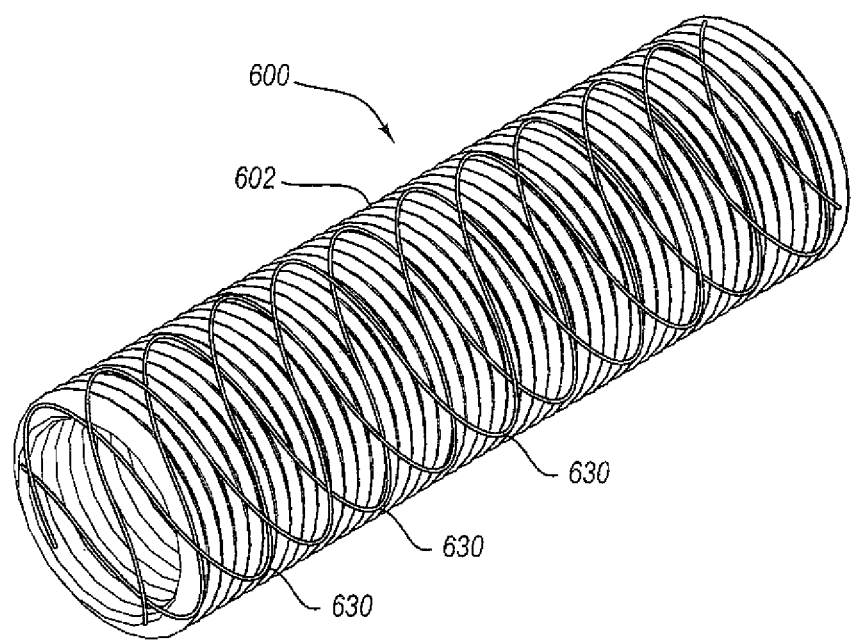
FIG. 59 is a perspective view of an exemplary reinforced conduit according to certain embodiments.

According to some embodiments, a conduit may be reinforced to provide additional strength and resistance to kinking. FIGS. 57-59 show examples of reinforced conduit 600. Conduit 600 may be a surgically implantable conduit. FIG. 57 illustrates conduit 600 with a duct 602 and reinforcing rings 610 that maintain a fixed diameter for the conduit 600. Duct 602 may comprise synthetic material (or any other suitable material) that forms the body of conduit 600, and rings 610 may provide rigid reinforcement for duct 602. The duct 602 is shown having a continuous tubular structure. Rings 610 may be made of any suitable material, including metal, plastic, or other synthetic materials. FIG. 58 illustrates conduit 600 with a reinforcing spiral 620. FIG. 59 illustrates conduit 600 with several reinforcing spirals 630 forming a reinforcing mesh. As shown in FIGS. 58 and 59, the reinforcing spirals 620, 630 extend along a single path between consecutive turns of the spiral shape. Any other suitable configuration of reinforcing members may be used to reinforce conduit 600.

Figure 60:
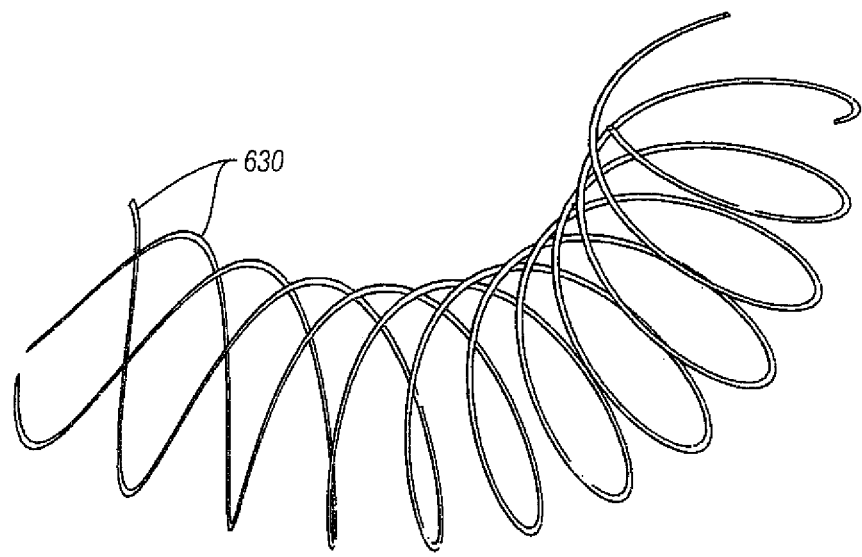
FIG. 60 is a perspective view of exemplary reinforcing members for a cardiovascular conduit.
Figure 61:
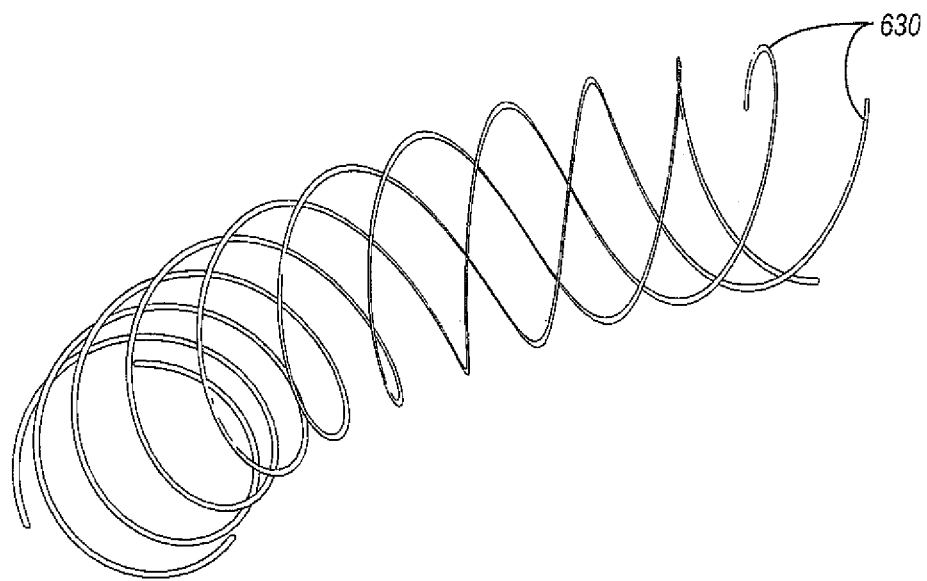
FIG. 61 is a perspective view of exemplary reinforcing members for a cardiovascular conduit.

Conduit reinforcement may be positioned on the interior or exterior of a duct. According to some embodiments, conduit reinforcement may be woven through duct material and/or sandwiched between two layers of duct. Conduit reinforcement may be pre-shaped to conform to a patient's anatomy, as shown in FIGS. 60 and 61. FIGS. 60 and 61 show how reinforcing spirals 630 may be pre-shaped to form a curved conduit section. The pre-shaped conduit may be bendable or may be rigid. For example, conduit may be shaped to curve around a patient's anatomy between the patient's heart and the patient's aorta. In other embodiments, conduit reinforcement may be a straight tube that is bendable to conform to a patient's anatomy.

The reinforced conduit shown in FIGS. 57-61 may be used with any of the connectors and/or conduit systems disclosed herein. The connectors, conduit, and conduit systems presented in the instant disclosure may provide better connections and stronger seals with cardiovascular organs. The systems and methods disclosed herein may also provide stronger and more flexible conduits and connector-conduit attachments than prior apical aortic conduits. Those of skill in the art will recognize that embodiments of the instant disclosure also provide various other advantages over prior systems and methods.

The preceding description has been provided to enable others skilled in the art to best utilize various aspects of the exemplary embodiments described herein. This exemplary description is not intended to be exhaustive or to be limited to any precise form disclosed. Many modifications and variations are possible without departing from the spirit and scope of the instant disclosure. It is desired that the embodiments described herein be considered in all respects illustrative and not restrictive and that reference be made to the appended claims and their equivalents for determining the scope of the instant disclosure.

Unless otherwise noted, the terms "a" or "an", as used in the specification and claims, are to be construed as meaning "at least one of." In addition, for ease of use, the words "including" and "having", as used in the specification and claims, are interchangeable with and have the same meaning as the word "comprising."

What is claimed is:

1. A cardiovascular conduit system comprising:
   a connector comprising:
   a proximal end adapted to attach to a cardiovascular organ, the proximal end comprising:
      a first plurality of expandable members, each member in the first plurality of expandable members being deployable from a delivery position having a cylindrical helical shape to a deployed position having a proximal-end planar spiral shape, the delivery position forming a circular passage through the connector, the first plurality of expandable members being dimensioned to deploy inside the cardiovascular organ to directly contact and secure the connector to the cardiovascular organ without any interposing material;
   a distal end adapted to have a conduit attached thereto;
   a mid-section between the distal and proximal ends, the mid-section comprising:
      a second plurality of expandable members extending from the mid-section, each member in the second plurality of expandable members being deployable from a delivery position to a deployed position having a mid-section planar spiral shape, the mid-section planar spiral shape extending from the mid-section between the distal end and the proximal end;
   an opening extending through the connector, the opening being dimensioned to transfer blood between the conduit and the cardiovascular organ, the proximal-end planar spiral shape and the mid-section planar spiral shape each being perpendicular to a longitudinal axis of the opening extending through the connector.

2. The cardiovascular conduit system of claim 1, further comprising a retractable retaining member that holds the first plurality of expandable members in the delivery position.

3. The cardiovascular conduit system of claim 2, wherein the first plurality of expandable members are spaced around a perimeter of the proximal end of the connector.

4. The cardiovascular conduit system of claim 1, wherein the first plurality of expandable members comprise at least one of: shape-memory wire, shape-memory tube, or shape-memory sheet.

5. The cardiovascular conduit system of claim 1, further comprising fabric extending between at least two expandable members in the first plurality of expandable members.

6. The cardiovascular conduit system of claim 1, wherein the connector comprises an apical connector.

7. The cardiovascular conduit system of claim 1, wherein the connector further comprises an expandable mid-section between the distal and proximal ends, the expandable mid-section being deployable to apply a radial force on an opening in the cardiovascular organ.

8. The cardiovascular conduit system of claim 1, wherein the connector is dimensioned to attach to a vascular organ.

9. The cardiovascular conduit system of claim 1, wherein the first plurality of expandable members forms a cylinder in the delivery position.

10. The cardiovascular conduit system of claim 1 wherein the second plurality of expandable members is deployable from a delivery position having a cylindrical helical shape, the second plurality of expandable members being dimensioned to deploy outside the cardiovascular organ to secure the connector to the cardiovascular organ.

11. The cardiovascular conduit system of claim 1, wherein each member in the first plurality of expandable members forms a spiral in the delivery position.

12. The cardiovascular conduit system of claim 1, further comprising at least one ring member extending around the conduit and positioned within a circumferential groove in the distal end of the connector, wherein the at least one ring member comprises a spring positioned around the conduit and seated in the circumferential groove of the connector to rotatably secure the conduit to the connector.

13. The cardiovascular conduit system of claim 12, wherein the at least one ring member comprises a ring positioned around the spring and seated in the circumferential groove of the connector.

14. The cardiovascular conduit system of claim 1, wherein the conduit comprises a duct and a reinforcing member.

15. The cardiovascular conduit system of claim 1, wherein the conduit is attached to an inside of the opening in the connector.

16. The cardiovascular conduit system of claim 1, wherein the conduit is attached to an outside of the connector.

17. The cardiovascular system of claim 1, wherein the connector comprises at least one of:
   a first cuff adapted to be positioned against an outside surface of the cardiovascular organ;
   a second cuff adapted to be positioned against an inside surface of the cardiovascular organ.

18. A cardiovascular conduit system comprising:
   a conduit;
   an apical connector attached to the conduit, the apical connector comprising:
   a first expandable member and a second expandable member, the first and second expandable members being deployable from a delivery configuration having a cylindrical helical shape forming a circular passage through the apical connector to a deployed configuration having a planar spiral shape, the planar spiral shape of the deployed configuration of the first and second expandable members being perpendicular to a longitudinal axis of the apical connector attached to the conduit;

wherein the conduit is connected to an outer surface of the apical connector at a distal end of the apical connector spaced distal of both the first expandable member and the second expandable member.

19. A cardiovascular conduit system comprising:
a first connector comprising:
a plurality of expandable members;
a proximal end dimensioned to be attached directly to a first cardiovascular organ with the plurality of expandable members and without any interposing material positioned between the cardiovascular organ and the expandable members;
a distal end having a circumferential groove formed therein, the circumferential groove having a radial depth;
a first conduit directly contacting and rotatably attached only to an exterior of the first connector only at the distal end with at least one ring member positioned around the first conduit and within the circumferential groove, the ring member having a width that is no greater than a width of the circumferential groove;
a first spring positioned around a first end of the first conduit and seated within the radial depth of the groove of the first connector to rotatably secure the first conduit to the first connector;
wherein the at least one ring member is positioned external to the first spring and seated within the radial depth of the groove of the first connector.

20. The cardiovascular conduit system of claim 19, wherein:
the first connector comprises a groove formed in the distal end;
the first conduit is positioned around an outside of the distal end of the first connector.

21. The cardiovascular conduit system of claim 19, further comprising:
a second connector comprising:
a proximal end dimensioned to be attached to a second cardiovascular organ;
a distal end;
a groove formed in the distal end of the second connector;
a second spring positioned around the second end of the first conduit and seated in the groove of the second connector to rotatably secure the first conduit to the second connector.

22. The cardiovascular conduit system of claim 21, wherein:
the first connector comprises an apical connector;
the second connector comprises an aortic connector.

23. The cardiovascular conduit system of claim 19, further comprising:
a second connector comprising:
a first end;
a second end;
a first groove formed in the first end of the second connector;
a second groove formed in the second end of the second connector;
a second conduit;
a second spring positioned around a second end of the first conduit and seated in the first groove of the second connector to rotatably secure the second connector to the first conduit;
a third spring positioned around a first end of the second conduit and seated in the second groove of the second connector to rotatably secure the second conduit to the second connector.

24. The cardiovascular conduit system of claim 23, further comprising:
a third connector comprising:
a proximal end dimensioned to be attached to a second cardiovascular organ;
a distal end;
a groove formed in the distal end of the third connector;
a fourth spring positioned around a second end of the second conduit and seated in the groove of the third connector.

25. A cardiovascular conduit system comprising:
a surgically implantable conduit comprising:
a duct having a continuous tubular structure with a fixed, non-collapsible diameter;
a spiral shaped reinforcing member attached to the duct and extending along a single path between consecutive turns of the spiral shaped reinforcing member.

26. The cardiovascular conduit system of claim 25, wherein the cardiovascular conduit system comprises a plurality of disconnected rings attached to the duct.

27. The cardiovascular conduit system of claim 25, wherein the surgically implantable conduit is pre-shaped to extend from an apex of a heart to an aorta.

28. The cardiovascular conduit system of claim 25, wherein the surgically implantable conduit is flexible.

* * * * *